US011878287B2

(12) United States Patent
Ali et al.

(10) Patent No.: US 11,878,287 B2
(45) Date of Patent: Jan. 23, 2024

(54) ACTIVE AND STABLE COPPER-BASED CATALYST FOR $CO_2$ HYDROGENATION TO METHANOL

(71) Applicant: QATAR UNIVERSITY, Doha (QA)

(72) Inventors: Sardar Ali, Doha (QA); Dharmesh Kumar, Doha (QA); Muftah El-Naas, Doha (QA)

(73) Assignee: QATAR UNIVERSITY, Doha (QA)

( * ) Notice: Subject to any disclaimer, the term of this patent is extended or adjusted under 35 U.S.C. 154(b) by 0 days.

(21) Appl. No.: 17/570,655

(22) Filed: Jan. 7, 2022

(65) Prior Publication Data
US 2022/0219147 A1 Jul. 14, 2022

Related U.S. Application Data

(60) Provisional application No. 63/136,542, filed on Jan. 12, 2021.

(51) Int. Cl.
B01J 21/04 (2006.01)
B01J 23/06 (2006.01)
B01J 23/10 (2006.01)
B01J 23/72 (2006.01)
B01J 23/80 (2006.01)
B01J 23/83 (2006.01)
B01J 35/02 (2006.01)
(Continued)

(52) U.S. Cl.
CPC .............. *B01J 23/83* (2013.01); *B01J 6/001* (2013.01); *B01J 21/04* (2013.01); *B01J 35/023* (2013.01); *B01J 35/1014* (2013.01); *B01J 37/04* (2013.01); *B01J 37/18* (2013.01); *C07C 29/154* (2013.01); *B82Y 30/00* (2013.01); *B82Y 40/00* (2013.01); *C07C 2523/83* (2013.01)

(58) Field of Classification Search
CPC ... B01J 21/04; B01J 23/06; B01J 23/10; B01J 23/72; B01J 23/80; B01J 23/83; B01J 35/023; B01J 35/1014; B01J 37/04; B01J 37/18
See application file for complete search history.

(56) References Cited

U.S. PATENT DOCUMENTS 5,691,268 A * 11/1997 Koveal .................... B01J 23/83 502/343
6,680,279 B2 * 1/2004 Cai ....................... B01J 35/1014 502/329

(Continued)

OTHER PUBLICATIONS

H. Arakawa et al., "Selective Conversion of CO2 to Methanol by Catalytic Hydrogenation over Promoted Copper Catalyst", Energy Convers. Mgmt vol. 33, No. 5-8, pp. 521-528, 1992, 8 pages.

(Continued)

*Primary Examiner* — Cam N. Nguyen
(74) *Attorney, Agent, or Firm* — SQUIRE PATTON BOGGS (US) LLP

(57) ABSTRACT

This invention relates to development of novel Cu-based nanocatalysts synthesized via one-pot solution combustion synthesis for $CO_2$ hydrogenation to methanol. The novel Cu-based catalyst has exceptional activity for $CO_2$ hydrogenation with high methanol selectivity in the reaction temperature range between 250° C.-350° C. The novel catalyst also exhibits excellent resilience to deactivation due to sintering.

24 Claims, 12 Drawing Sheets

(51) Int. Cl.
- *B01J 35/10* (2006.01)
- *B01J 37/04* (2006.01)
- *B01J 37/18* (2006.01)
- *B01J 6/00* (2006.01)
- *C07C 29/154* (2006.01)
- *B82Y 40/00* (2011.01)
- *B82Y 30/00* (2011.01)

(56) References Cited

U.S. PATENT DOCUMENTS

| | | | | |
|---|---|---|---|---|
| 7,098,167 | B2* | 8/2006 | Watson | B01J 20/08 |
| | | | | 502/345 |
| 7,501,112 | B2* | 3/2009 | Watson | B01J 20/0255 |
| | | | | 423/655 |
| 10,533,987 | B2* | 1/2020 | Kim | B01J 35/0033 |
| 10,695,749 | B2* | 6/2020 | Xiao | B01J 23/60 |
| 10,858,302 | B2* | 12/2020 | Chen | B01J 23/80 |
| 10,919,026 | B2* | 2/2021 | Xiao | B01J 23/89 |
| 11,033,880 | B2* | 6/2021 | Mukherjee | B01J 37/0207 |
| 11,040,331 | B2* | 6/2021 | Mukherjee | B01J 37/036 |
| 11,478,778 | B2* | 10/2022 | Mukherjee | B01J 23/30 |
| 2019/0076828 | A1* | 3/2019 | Almusaiteer | B01J 23/80 |
| 2021/0322958 | A1* | 10/2021 | Huang | B01J 35/023 |
| 2022/0088572 | A1* | 3/2022 | Qi | B01D 53/8678 |

OTHER PUBLICATIONS

Hasliza Behruji et al., "Pd/ZnO Catalysts for Direct CO2 Hydrogenation to Methanol", Journal of Catalysis 343 (2016) 133-146, www.elsevier.com/locate/jcat, http://dx.doi.org/10.1016/j.jcat.2016.03.017, 14 pages.

Anatasiya Bavykina et al., "Turning a Methanation Co Catalyst into an In—Co Methanol Producer", ACS Catalysis 2019, 9, 6910-6918, pubs.acs.org/acscatalysis, DOI: 10.1021/acscatal.9b01638, 9 pages.

G. Bonura et al., "The Changing Nature of the Active Site of Cu—Zn—Zr Catalysts for the CO2 Hydrogenation reaction to Methanol", Applied Catalysis B: Environmental 152-153 (2014) 152-161, www.elsevier.com/locate/apcatb, http://dx/doi.org/10.1016/j.apcatb.2014.01.035, 10 pages.

Weijie Cai et al., "CO2 Hydrogenation to Methanol over CuZnGa Catalysts Prepared Using Microwave-assisted Methods", Catalysis Today 242 (2015) 193-199, www.elsevier.com/locate/cattod, http://dx.doi.org/10.1016/j.cattod.2014.06.012, 7 pages.

Kun Chen et al., "CO2 Hydrogenation to Methanol over Cu Catalysts Supported on La-modified SBA-15: The Crucial Role of Cu—LaOx Interfaces", Applied Catalysis B: Environmental 251 (2019) 119-129, www.elsevier.com/locate/apcatb, https://doi.org/10.1016/j.apcatb.2019.03.059, 11 pages.

Chen-Yu Chou et al., "Direct Conversion of CO2 into Methanol Over Promoted Indium Oxide-based Catalysts", Applied Catalysis A, General 583 (2019) 117144, www.elsevier.com/locate/apcata, https://doi.org/01.1016/j.apcata.2019.117144, 9 pages.

Varisara Deerattrakul et al., "The Roles of Nitrogen Species on Graphene Aerogel Supported Cu—Zn as Efficient Catalysts for CO2 Hydrogenation to Methanol", Applied Catalysis A, General 580 (2019) 46-52, www.elsevier.com/locateapcata, https://doi.org/10.1016/j.apcata.2019.04.030, 7 pages.

Xin Fang et al., Improved methanol yield and selectivity from CO2 Hydrogenation Using a Novel Cu—ZnO—ZrO2 Catalyst Supported on Mg-A1 layered double hydroxide (LDH), Journal of CO2 Utilization 29 (2019) 57-64, www.elsevier.com/locate/jcou, https://doi.org/10.1016/j.jcou.2018.11.006, 8 pages.

Peng Gao et al., "Fluorinated Cu/Zn/A1/Zr Hydrotalcites Derived Nanocatalysts for CO2 Hydrogenation to Methanol", Journal of CO2 Utilization 16 (2016) 32-41, www.elsevier.com/locate/jcou, http://dx.doi.org/01.1016/j.jcou.2016.06.001, 10 pages.

Bing Hu et al., "Hydrogen Spillover Enabled Active Cu Sites for Methanol Synthesis From CO2 Hydrogenation Oveer Pd Doped CuZn Catalysts", Journal of Catalysis 359 (2018) 17-26, www.elsevier.com/locate/jcat, https://doi.org/10.1016/j.jcat.2017.12.029, 10 pages.

Haoxi Jiang et al., "Efficient Hydrogenation of CO2 to Methanol Over Pd/In2O3/SBA-15 Catalysts", Journal of CO2 Utilization 36 (2020) 33-39, www.elsevier.com/locate/jcou, https://doi.org/10.1016/j.jcou.2019.10.013, 7 pages.

Shaozhong Li et al., "A Highly Active and Selective Mesostructured Cu/A1CeO Catalyst for CO2 Hydrogenation to Methanol", Applied Catalysis A, General 571 (2019) 51-60, www.elsevier.com/locate/apcata, https://doi.org/10.1016/j.apcata.2018.12.008, 10 pages.

Shaozhong Li et al., "Hydrogenation of CO2 to Methanol Over Cu/AlCeO Catalyst", Catalysis Today 339 (2020) 352-361, www.elsevier.com/locate/cattod, https://doi.org/10.1016/j.cattod.2019.01.015, 10 pages.

Alexey Pustovarenko et al., "Metal-Organic Framework-Derived Synthesis of Cobalt Indium Catalysts for the Hydrogenation of CO2 to Methanol", ACS Catalysis, pubs.acs.org/acscatalysis, https://dx.doi.org/10.1021/acscatal.0c00449, 13 pages.

Ning Rui et al., "CO2 Hydrogenation to Methanol over Pd/In2O3: Effects of Pd and Oxygen Vacancy", Applied Catalysis B: Environmental 218 (2017) 488-497, www.elsevier.com/locate/apcatb, http://dx.doi.org/10.1016/j.apcatb.2017.06.069, 10 pages.

Kaihang Sun et al., "Hydrogenation of CO2 to Methanol over In2O3 Catalyst", Journal of CO2 Utilization 12 (2015) 1-6, www.elsevier.com/locate/jcou, http://dx.doi.org/10.1016/j.jcou.2015.09.002, 6 pages.

Xiuxiu Wang et al., "A Novel Microreaction Strategy to Fabricate Superior Hybrid Zirconium and Zinc Oxides for Methanol Synthesis from CO2", Applied Catalysis A, General 595 (2020) 117507, www.elsevier.com/locate/apcata, https://doi.org/10.1016/j.apcata.2020.117507, 9 pages.

Haijuan Zhan et al., "Structural Properties and Catalytic Performance of the La—Cu—Zn Mixed Oxides for CO2 Hydrogenation to Methanol", Journal of Rare Earths 36 (2018) 273-280, www.journals.elsevier.com/journal-of-rare-earths, http://dx.doi.org/10.1016/j.jre.2017.07.017, 8 pages.

* cited by examiner

ACTIVE AND STABLE COPPER-BASED CATALYST FOR $CO_2$ HYDROGENATION TO METHANOL

This application claims priority to, and the benefit of, U.S. Provisional Patent Application No. 63/136,542 filed Jan. 12, 2021. The entirety of this application is incorporated herein by reference for all purposes.

FIELD

This invention relates to novel lanthanum oxide-promoted Cu-based nanocomposite catalysts, their synthesis via a simple one-pot solution combustion synthesis, and their use for $CO_2$ hydrogenation to methanol.

BACKGROUND

The world's energy demand, fueled by population growth and improved standards of living is expected to double by 2100 and the Intergovernmental Panel on Climate Change (IPCC) study showcases that as anthropogenic $CO_2$ emissions continues to rise, this results in $CO_2$ pollution into the atmosphere. For this reason, population growth should be met responsibly and sustainably by managing $CO_2$ emissions. With the aim to contain these emissions, Global $CO_2$ Initiative (GCI) proposed reduction in $CO_2$ emissions by its capture and/or its re-use. This initiative was structured to accelerate innovation and development in carbon capture and its utilization (CCUS), with the goal of commercializing $CO_2$-based products to result in the reduction of carbon dioxide emissions and create value out of waste. Currently, efforts are being made to develop promising catalysts for the thermochemical and/or electrochemical reduction of $CO_2$ into useful products, such as methanol. However, an efficient and cost-effective catalyst for $CO_2$ hydrogenation to methanol is yet to be developed. This is mainly due to the following:

(i) Activity and methanol selectivity of the catalysts under moderate pressure and temperature is low and/or limited. This is because of the existence of the endothermic reverse water gas shift (RWGS) reaction that can produce carbon monoxide;
(ii) Catalysts experience deactivation with time on stream if the gaseous feed is based on pure $CO_2$; and
(iii) High reaction temperatures (>280° C.) are often required to achieve better $CO_2$ conversion, which in turn leads to a significant decrease in methanol selectivity and deactivation of the catalyst, as well as the formation of undesirable $CH_4$ production.

The object of this invention is to provide an improved, active, and stable catalyst for $CO_2$ hydrogenation to methanol that yields high amounts of methanol, no significant amount of $CH_4$, and exhibits high selectivity for methanol under both moderate and high temperature and pressure conditions.

SUMMARY

Described herein are novel lanthanum oxide-promoted Cu-based nanocomposite catalysts that demonstrate excellent catalytic performance for the $CO_2$ hydrogenation to methanol. The catalysts are stable and highly active for $CO_2$ conversion in both moderate to high temperature and pressure ranges (about 250° C. to 350° C. and about 60 to 85 bars), yielding significantly high amounts of methanol. In certain embodiments, the catalysts as described herein exhibit a high methanol yield of about 2.45 $g_{MeOH} g_{cat}^{-1} h^{-1}$ when exposed to a temperature of about 325° C., a pressure of about 85 bars, and a gas hourly space velocity of about 55,000 $h^{-1}$.

The catalysts are also highly selective for methanol, and during the catalytic conversion, produce no significant amounts of undesirable $CH_4$. Importantly, in certain embodiments, even at high operating temperatures of 350° C., no $CH_4$ is produced. A catalyst that exhibits stability and catalytic activity under both moderate and high temperatures is advantageous. Activity under moderate or mild conditions involves less energy consumption and stability under high conditions allows for increased MeOH production without the expected loss in selectivity and increase in undesired byproducts.

In one embodiment, the nanocomposite catalyst for $CO_2$ hydrogenation to methanol is an efficient and stable alumina supported copper and zinc nanocatalyst with a copper loading in the range of about 10 wt % to 60 wt % promoted with lanthanum oxide in the range of about 0.5 wt % to 10 wt %.

The active and stable catalyst and the efficient catalytic performance is attributed to various unique physicochemical properties, such as the presence of oxygen vacancies and/or surface defects, smaller metal particles size, and good dispersion. The formate pathway and the reverse water gas shift reaction (RWGS) pathway are two established pathways for $CO_2$ hydrogenation to methanol. The catalysts described herein exhibit improved conversion of $CO_2$ because once the overall reactions start by chemisorption of $H_2$ on the surface of copper, the $CO_2$ is chemisorbed onto the surface of ZnO and/or oxygen vacancy/defects. Further, the catalysts as described herein exhibit improved MeOH selectivity over carbon monoxide and high yield by improving adsorption of the formate intermediate during the formate pathway. In the absence of these surface defects, MeOH selectivity is expected to be lower as adsorption of the formate intermediate will be poor and the catalyst will tend to produce more CO. These properties make the catalysts important materials for various industrial and technological applications.

Also described herein is a method for the synthesis of lanthanum oxide promoted Cu-based nanocomposite catalysts supported on alumina via a single-step solution combustion synthesis. This simple one-step reaction results in the creation of more oxygen vacancies and/or surface defects due to the incorporation of lanthanum oxide-induced electronic modifications. In one embodiment, the single-step solution combustion synthesis is conducted in a batch size of about 10 g. In one embodiment, the synthesis affords an efficient and stable alumina supported copper and zinc nanocatalyst with a copper loading in the range of about 10 wt % to 60 wt % promoted with lanthanum oxide in the range of about 0.5 wt % to 10 wt %.

Also described herein is a method of hydrogenating $CO_2$ to methanol using the catalyst as described herein. In certain embodiments, the catalyst exhibits a high $CO_2$ conversion of about 30%, a selectivity for MeOH of about 42 wt %, and a methanol yield of about 2.45 $g_{MEOH} g_{cat}^{-1} h^{-1}$ when the catalyst is exposed to a temperature of about 325° C., a pressure of about 85 bars, and a gas hourly space velocity of about 55,000 $h^{-1}$.

In certain embodiments, the material disclosed herein can be employed as a heterogeneous catalyst for various industrial processes, including, but not limited to, hydrogenation reactions, for example, hydrogenation of $CO_2$ to methanol and hydrogenation of $CO_2$ and/or CO to light olefins and paraffins.

BRIEF DESCRIPTION OF THE FIGURES

As shown in FIGS. 3A-3C, a fuel deficient mixture (lower G/O molar ratio) resulted in smaller average particle size. For example, the sample prepared with G/O molar ratio of 0.206 (FIG. 3C) resulted in an average particle size of 6.4 nm. TEM analysis affirmed XRD findings of FIGS. 5A and 5B.

As shown in FIG. 4A and FIG. 4B, particle size increases with the calcination temperature, which may be due to agglomeration. Calcination at 400° C. was effective for combustion and resulted in a minimal increase in particle size. TEM analysis affirmed XRD findings of FIGS. 5A and 5B.

FIG. 4B is a TEM image and analysis of the 30 wt % CuO/50 wt % ZnO/1 wt % $La_2O_3$/$Al_2O_3$ catalyst produced with a glycine/oxidant molar ratio (G/O) of 0.206 calcined at 600° C. as described in Example 2. TEM analysis affirmed XRD findings of FIGS. 5A and 5B.

FIG. 5A and FIG. 5B demonstrate the effects of lanthanum oxide incorporation into the catalyst. As shown in FIG. 5B compared to FIG. 5A, with incorporation of lanthanum oxide, an increase in the percentage of induced phases was recorded. The percentage of these phases in FIG. 5A and FIG. 5B is calculated based on total area of the integrated peaks.

As shown in FIG. 7 compared to FIG. 6, a shift in reduction temperature to higher degrees was recorded for the lanthanum oxide promoted catalyst, indicating an increase in stronger metal support interaction and the presence of surface defects and/or oxygen vacancies.

DETAILED DESCRIPTION

Figure 1:
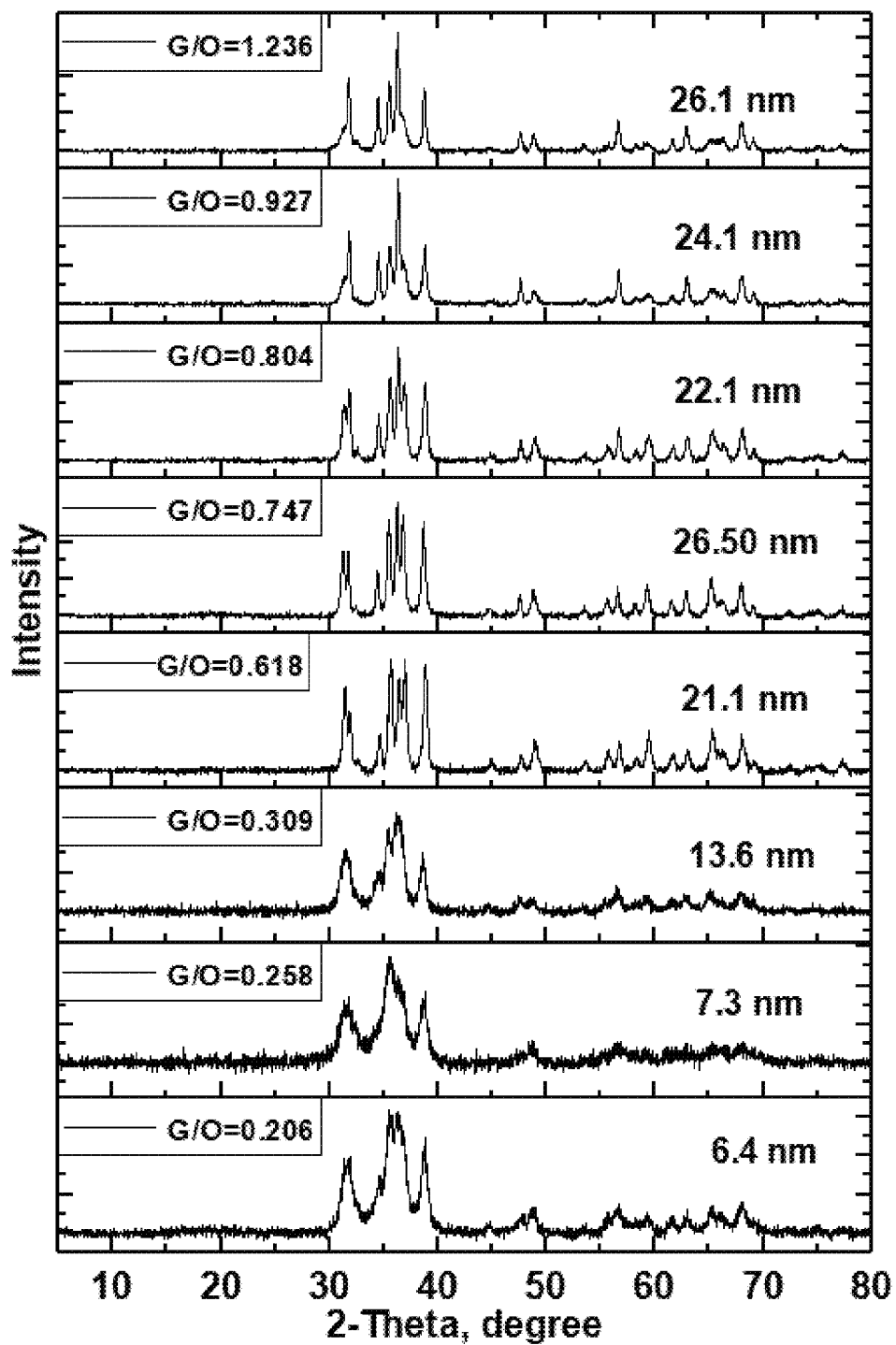
FIG. 1 provides X-ray diffraction patterns of unpromoted 30 wt % CuO/50 wt % ZnO/$Al_2O_3$ catalysts synthesized at various glycine/oxidant (G/O) molar ratios as described in Example 1.

Described herein is a novel lanthanum oxide-promoted Cu-based nanocomposite catalyst that demonstrates excellent catalytic performance for $CO_2$ hydrogenation to methanol. The catalyst is highly active for $CO_2$ conversion and yields high amounts of methanol in the temperature range of 250° C. to 350° C. and a pressure range of 60 to 85 bars. Furthermore, the catalyst is highly selective for methanol, and during the catalytic conversion, produces no significant amount of the undesirable byproduct $CH_4$.

Definitions

The terms "a" and "an" do not denote a limitation of quantity, but rather denote the presence of at least one of the referenced item. The term "or" means "and/or". Recitation of ranges of values merely intend to serve as a shorthand method of referring individually to each separate value falling within the range, unless otherwise indicated herein, and each separate value is incorporated into the specification as if it were individually recited herein. The endpoints of all ranges are included within the range and independently combinable. All processes described herein can be performed in a suitable order unless otherwise indicated herein or otherwise clearly contradicted by context. The use of example, or exemplary language (e.g., "such as"), is intended merely to better illustrate the invention and does not pose a limitation on the scope of the invention on unless otherwise claimed.

"Stability" is the ability of a catalyst to resist or be resilient to deactivation due to surface changes. Stability is quantified by measuring $CO_2$ conversion and MeOH selectivity as reaction time proceeds. Under given conditions of pressure, temperature and gaseous feed, a stable catalyst will exhibit no change in $CO_2$ conversion and MeOH selectivity. Changes in conversion and/or selectivity indicate surface changes of the catalyst.

"Gas hourly space velocity" (GHSV) or "space velocity" is the relation between volumetric flow rate and reactor volume of the catalyst. It signifies how many volumes of feed can be fed in a unit time through the volume of the catalyst and is calculated by the following equation: volumetric flow rate of gas/external volume of the catalyst monolith.

"Nanoparticle" as used herein, generally refers to a particle having a diameter, such as an average diameter in the range of about 1 nm to 100 nm, for example, from about 3 nm to about 20 nm. The particles can have any shape. Nanoparticle size is calculated using Debye Scherrer's equation from the XRD spectrum using the most intense peak measured full width at half maxima).

"Nanocatalyst" or "nanocomposite catalyst" is a catalyst where the active components/metals are in the range of about 1 nm to 100 nm, preferably dispersed over a porous support.

"Sintering" refers to agglomeration due to surface migration of the active metal particles. This results in the loss of the active metal surface in the catalyst and a decrease in activity.

Lanthanum Oxide-Promoted Cu-Based Catalysts

In one embodiment, the lanthanum oxide-promoted Cu-based nanocomposite catalyst comprises:
  (a) Nanoparticulates in the size range of about 3 nm to 20 nm comprising:
    (1) a copper oxide loading of about 20% wt % to 60 wt %;
    (2) a zinc oxide of about loading of about 40 wt % to 65 wt %; and
    (3) a lanthanum oxide with a loading of about 0.5 wt % to 10%; and,
  (b) Alumina as support.

In another embodiment, the lanthanum oxide-promoted Cu-based catalyst comprises:
  (a) Nanoparticulates in the size range of about 3 nm to 20 nm comprising:
    (1) a copper oxide loading of about 30% wt % to 60 wt %;
    (2) a zinc oxide loading of about 50 wt % to 62 wt %; and
    (3) a lanthanum oxide loading between about 0.5 wt % to 10%; and,
  (b) Alumina as support.

In another embodiment, the lanthanum oxide-promoted Cu-based catalyst comprises:
  (a) Copper oxide nanoparticles in the size range of about 3 nm to 20 nm with a copper loading of 30 wt % to 60 wt %;
  (b) Zinc oxide with a loading of 50 wt % to 62 wt %;
  (c) Lanthanum oxide with a loading in the range between 0.5 wt % and 10 wt %; and
  (d) Alumina as support.

In certain embodiments, the catalyst is characterized by a copper oxide loading in the range of about 20 wt % to 60 wt %. In certain embodiments, the catalyst is characterized by a copper oxide loading in the range of about 30 wt % to 60 wt %. In certain embodiments, the catalyst is characterized by copper oxide loading in the range of about 20 to 50 wt %, about 20 to 40 wt %, about 25 wt % to 40 wt %, about 30 wt % to 50 wt %, or about 20 wt % to 35 wt %. In a preferred embodiment, the catalyst is characterized by a copper oxide loading of about 30 wt %.

In certain embodiments, including any of the foregoing, the catalyst is characterized by a zinc oxide loading in the range of about 40 wt % to 65 wt %. In certain embodiments, including any of the foregoing, the catalyst is characterized by a zinc oxide loading in the range of about 50 wt % to 62 wt %. In certain embodiments, including any of the foregoing, the catalyst is characterized by a zinc oxide loading in the range of about 40 wt % to 60 wt %, about 40 wt % to 50 wt %, or about 50 wt % to 60 wt %. In a preferred embodiment, the catalyst is characterized by a zinc oxide loading of about 50 wt %.

In certain embodiments, including any of the foregoing, the catalyst is characterized by a lanthanum oxide loading in the range of about 0.5 wt % to 10.0 wt %. In certain embodiments, including any of the foregoing, the catalyst is characterized by a lanthanum oxide loading in the range of about 0.5 wt % to 8.0 wt %, about 0.5 wt % to 6.0 wt %, about 0.5 wt % to 4.0, about 0.5 wt % to 2.0 wt %, or about 0.5 wt % to 1.5 wt %. In certain embodiments, including any of the foregoing, the catalyst is characterized by a lanthanum oxide loading in the range of about 0.5 wt % to 3.0 wt %. In one embodiment, including any of the foregoing, the catalyst is characterized by a lanthanum oxide loading of at least about 0.5 wt %. In one embodiment, including any of the foregoing, the catalyst is characterized by a lanthanum oxide loading of less than about 10 wt %. In a preferred embodiment, including any of the foregoing, the catalyst is characterized by a lanthanum oxide loading of about 1 wt %.

In certain embodiments, including any of the foregoing, the catalyst comprises between about 20 wt % to 60 wt % of copper oxide, between about 40 wt % to 65 wt % of zinc oxide, and between about 0.5 wt % to 10 wt % of lanthanum oxide. In certain embodiments, including any of the foregoing, the catalyst comprises between about 30 wt % to 60 wt % of copper oxide, between about 50 wt % to 62 wt % of zinc oxide, and between about 0.5 wt % to 10 wt % of lanthanum oxide. In certain embodiments, the catalyst comprises about 30 wt % of copper oxide, about 50 wt % of zinc oxide, and about 1 wt % of lanthanum oxide.

In one embodiment, including any of the foregoing, the catalyst comprises between about 20 wt % to 60 wt % of copper oxide, between about 40 wt % to 65 wt % of zinc oxide, and between about 0.5 wt % to 10 wt % of lanthanum oxide on $Al_2O_3$ support. In one embodiment, including any of the foregoing, the catalyst comprises between about 30 wt % to 60 wt % of copper oxide, between about 50 wt % to 62 wt % of zinc oxide, and between about 0.5 wt % to 10 wt % of lanthanum oxide on $Al_2O_3$ support. In one embodiment, including any of the foregoing, the catalyst comprises about 30 wt % of copper oxide, about 50 wt % of zinc oxide, and about 1 wt % of lanthanum oxide on $Al_2O_3$ support.

In certain embodiments, including any of the foregoing, the nanoparticles of the nanocomposite catalyst described herein range from about 3 nm to 20 nm in diameter. In certain embodiments, including any of the foregoing, the nanoparticles of the nanocomposite catalyst described herein range from about 3 nm to 18 nm, from about 3 nm to 15 nm, from about 3 nm to 10 nm, from about 3 nm to 8 nm, or from about 3 nm to 6 nm in diameter. In certain embodiments, including any of the foregoing, the nanoparticles of the nanocomposite catalyst described herein range from about 3.87 nm to 18.1 nm in diameter. In certain embodiments, including any of the foregoing, the nanoparticles of the nanocomposite catalyst described herein is about 4 nm, about 4.5 nm, about 5 nm, about 7 nm, or about 18 nm in diameter. In one embodiment, including any of the foregoing, the nanoparticles of the nanocomposite catalyst described herein is about 3.9 nm, about 4.5 nm, about 5.0 nm, about 7.4 nm, or about 18.1 nm in diameter.

In certain embodiments, including any of the foregoing, the nanocomposite catalyst described herein is characterized by a BET surface area of between about 60 and 80 m$^2$/g. In certain embodiments, including any of the foregoing, the catalyst is characterized by a BET surface area of between about 70 and 80 m$^2$/g. In certain embodiments, including any of the foregoing, the catalyst is characterized by a BET surface area of between about 75 and 80 m$^2$/g. In one embodiment, including any of the foregoing, the catalyst is characterized by a BET surface area of about 77 m$^2$/g.

The Cu-based nanocomposite catalysts as described herein exhibit superior activity and stability during $CO_2$ hydrogenation. In certain embodiments, including any of the foregoing, the catalyst is stable during $CO_2$ hydrogenation to methanol in a temperature range between about 200° C. to 400° C. In certain embodiments, including any of the foregoing, the catalyst is stable during $CO_2$ hydrogenation to methanol in a temperature range between about 250° C. to 350° C. In certain embodiments, including any of the foregoing, the catalyst is stable during $CO_2$ hydrogenation to methanol up to a temperature of about 350° C. or about 400° C. In certain embodiments, including any of the foregoing, the catalyst is stable during $CO_2$ hydrogenation to methanol at a temperature greater than about 200° C. or about 250° C.

In certain embodiments, including any of the foregoing, the catalyst is stable during $CO_2$ hydrogenation to methanol at a pressure range between about 50 bars to 90 bars. In certain embodiments, including any of the foregoing, the catalyst is stable during $CO_2$ hydrogenation to methanol at a pressure range between about 60 bars to 85 bars. In certain embodiments, including any of the foregoing, the catalyst is stable during $CO_2$ hydrogenation to methanol at a pressure range between about 60 bars to 70 bars or between about 70 bars to 85 bars. In certain embodiments, including any of the foregoing, the catalyst is stable during $CO_2$ hydrogenation to methanol at a pressure range up to about 90 bars. In certain embodiments, including any of the foregoing, the catalyst is stable during $CO_2$ hydrogenation to methanol at a pressure range greater than about 50 bars.

In certain embodiments, including any of the foregoing, the catalyst is stable during $CO_2$ hydrogenation to methanol at a gas hourly space velocity (GHSV) range of about 7,000 h$^{-1}$ to 55,000 h$^{-1}$. In certain embodiments, including any of the foregoing, the catalyst is stable during $CO_2$ hydrogenation to methanol at a GHSV range of between about 7,000 h$^{-1}$ to 10,000 h$^{-1}$, between about 10,000 h$^{-1}$ to 15,000 h$^{-1}$, between about 15,000 h$^{-1}$ to 20,000 h$^{-1}$, between about 20,000 h$^{-1}$ to 25,000 h$^{-1}$, between about 25,000 h$^{-1}$ to 30,000 h$^{-1}$, between about 30,000 h$^{-1}$ to 35,000 h$^{-1}$, between about 35,000 h$^{-1}$ to 45,000 h$^{-1}$, between about 45,000 h$^{-1}$ to 50,000 h$^{-1}$, or between about 50,000 h$^{-1}$ to 55,000 h$^{-1}$. In certain embodiments, including any of the foregoing, the catalyst is stable during $CO_2$ hydrogenation to methanol at a GHSV range of between about 27,000 h$^{-1}$ to 55,000 h$^{-1}$. In certain embodiments, including any of the foregoing, the catalyst is stable during $CO_2$ hydrogenation to methanol at a GHSV range of greater than about 7,000 h$^{-1}$. In certain embodiments, including any of the foregoing, the catalyst is stable during $CO_2$ hydrogenation to methanol at a GHSV range of less than about 55,000 h$^{-1}$.

In certain embodiments, including any of the foregoing, the catalyst is stable during $CO_2$ hydrogenation to methanol at molar ratio of $H_2:CO_2$ in the range of about 2:1 to 5:1. In certain embodiments, including any of the foregoing, the catalyst is stable during $CO_2$ hydrogenation to methanol at molar ratio of $H_2:CO_2$ in the range of about 3:1 to 4:1. In certain embodiments, including any of the foregoing, the catalyst is stable during $CO_2$ hydrogenation to methanol at molar ratio of $H_2:CO_2$ in the range of about 3:1. In certain embodiments, including any of the foregoing, the catalyst is stable during $CO_2$ hydrogenation to methanol at molar ratio of $H_2:CO_2$ in the range of about 3.4:1. In certain embodiments, including any of the foregoing, the catalyst is stable during $CO_2$ hydrogenation to methanol at molar ratio of $H_2:CO_2$ in the range of about 4:1.

Further, in certain embodiments, including any of the foregoing, the catalyst as described herein is stable under the conditions described herein for a period of at least about 4,000 hours, about 6,000 hours, about 8,000 hours, about 9,000 hours, about 10,000 hours, about 12,000 hours, about 14,000 hours, or more. In certain embodiments, including any of the foregoing, the catalyst is stable under the conditions as described herein for a period of at least about 1,200 hours or more. In one embodiment, including any of the foregoing, the catalyst is stable under the conditions as described herein for a period of at least about 1,400 hours or more.

In one embodiment, including any of the foregoing, the catalyst is stable during $CO_2$ hydrogenation to methanol in a temperature range between about 250° C. to 350° C., a pressure range between about 60 bars to 85 bars, a gas hourly space velocity (GHSV) range of about 7,000 h$^{-1}$ to 55,000 h$^{-1}$ and a molar ratio of $H_2:CO_2$ in the range of about 3:1 to 4:1. In one embodiment, including any of the foregoing, the catalyst is characterized by a BET surface area of about 77 m$^2$/g and is stable during $CO_2$ hydrogenation to methanol in a temperature range between about 250° C. to 350° C., a pressure range between about 60 bars to 85 bars, a space velocity range of about 7,000 h$^{-1}$ to 55,000 h$^{-1}$ and molar ratio of $H_2:CO_2$ in the range of about 3:1 to 4:1.

In certain embodiments, including any of the foregoing, the catalyst is stable during $CO_2$ hydrogenation to methanol for at least about 14,000 hours in a temperature range between about 250° C. to 350° C., a pressure range between about 60 bars to 85 bars, a space velocity range of about 7,000 h$^{-1}$ to 55,000 h$^{-1}$ and a molar ratio of $H_2:CO_2$ in the range of about 3:1 to 4:1. In certain embodiments, including any of the foregoing, the catalyst is characterized by a BET surface area of about 77 m$^2$/g and is stable during $CO_2$ hydrogenation to methanol for at least about 14,000 hours in a temperature range between about 250° C. to 350° C., a pressure range between about 60 bars to 85 bars, a space velocity range of about 7,000 h$^{-1}$ to 55,000 h$^{-1}$ and a molar ratio of $H_2:CO_2$ in the range of about 3:1 to 4:1.

In one embodiment, including any of the foregoing, the catalyst is stable during $CO_2$ hydrogenation to methanol for at least about 14,000 hours in a temperature range between about 250° C. to 350° C., a pressure range between about 60 bars to 85 bars, a space velocity range of about 5,000 h$^{-1}$ to 5,500 h$^{-1}$ and a molar ratio of $H_2:CO_2$ in the range of about 3.4:1 to 4:1.

In certain embodiments, the catalyst as described herein exhibits excellence resilience to deactivation due to sintering. In certain embodiments, including any of the foregoing, the catalyst exhibits reliance to deactivation for a period of at least about 4.00 hours, about 6,000 hours, about 8,000 hours, about 9,000 hours, about 10,000 hours, about 12,000 hours, about 14,000 hours, or more. In certain embodiments, including any of the foregoing, the catalyst exhibits resilience to deactivation for a period of at least about 1,200 hours or more. In one embodiment, including any of the foregoing, the catalyst exhibits resilience to deactivation for a period of at least about 1,400 hours or more.

A Method of $CO_2$ Hydrogenation to Methanol Using Lanthanum Oxide-Promoted Cu-Based Catalysts Further, in certain embodiments, including any of the foregoing, the catalyst as described herein does not produce methane ($CH_4$) as an undesired byproduct. In one embodiment, including any of the foregoing, the catalyst does not produce methane as an undesired byproduct at a temperature of at least about 350° C. In one embodiment, including any of the foregoing, the catalyst does not produce methane as an undesired byproduct at a temperature of about 350° C.

In one embodiment, including any of the foregoing, the catalyst as described herein exhibits a methanol yield of about 1.0 $g_{MeOH}$ $g_{cat}^{-1}$ $h^{-1}$. In one embodiment, including any of the foregoing, the catalyst as described herein exhibits a methanol yield of about 1.5 $g_{MeOH}$ $g_{cat}^{-1}$ about 2.0 $g_{MeOH}$ $g_{cat}^{-1}$ $h^{-1}$, about 2.5 $g_{MeOH}$ $g_{cat}^{-1}$ $h^{-1}$, about 3.0 $g_{MeOH}$ $g_{cat}^{-1}$ $h^{-1}$, about 5.0 $g_{MeOH}$ $g_{cat}^{-1}$ $h^{-1}$, or about 6.0 $g_{MeOH}$ $g_{cat}^{-1}$ $h^{-1}$. In one embodiment, including any of the foregoing, the catalyst as described herein exhibits a methanol yield of about 2.45 $g_{MeOH}$ $g_{cat}^{-1}$ $h^{-1}$.

In one embodiment, including any of the foregoing, the catalyst as described herein exhibits a conversion of $CO_2$ of greater than about 10%, greater than about 20%, greater than about 30%, greater than about 40%, greater than about 50%, greater than about 60%, or higher. In one embodiment, including any of the foregoing, the catalyst as described herein exhibits a conversion of $CO_2$ of about 30%.

In one embodiment, including any of the foregoing, the catalyst as described herein exhibits a selectivity for MeOH over carbon monoxide of greater than about 10 wt %, greater than about 20 wt %, greater than about 30 wt %, greater than about 40 wt %, greater than about 50 wt %, greater than about 60 wt %, or higher. In one embodiment, including any of the foregoing, the catalyst as described herein exhibits a selectivity for MeOH over carbon monoxide between about 40 wt % and 45 wt %. In one embodiment, including any of the foregoing, the catalyst as described herein exhibits a selectivity for MeOH over carbon monoxide of about 42 wt %.

In one embodiment, including any of the foregoing, the catalyst as described herein comprises between about 30 wt % to 60 wt % of copper oxide, between about 50 wt % to 62 wt % of zinc oxide, and between about 0.5 wt % to 10 wt % of lanthanum oxide on $Al_2O_3$ support and exhibits a $CO_2$ conversion of about 30% with a MeOH selectivity over carbon monoxide of about 42 wt % and a methanol yield of about 2.45 $g_{MeOH}$ $g_{cat}^{-1}$ $h^{-1}$.

In one embodiment, including any of the foregoing, the catalyst as described herein comprises between about 30 wt % to 60 wt % of copper oxide, between about 50 wt % to 62 wt % of zinc oxide, and about 1.0 wt % of lanthanum oxide on $Al_2O_3$ support and exhibits a $CO_2$ conversion of about 30% with a MeOH selectivity over carbon monoxide of about 42 wt % and a methanol yield of about 2.45 $g_{MeOH}$ $g_{cat}^{-1}$ $h^{-1}$.

In one embodiment, including any of the foregoing, the catalyst as described herein comprises about 30 wt % CuO/50 wt % ZnO/1 wt % $La_2O_3$ by weight on $Al_2O_3$ support and exhibits a $CO_2$ conversion of about 30% with a MeOH selectivity over carbon monoxide of about 42 wt % and a methanol yield of about 2.45 $g_{MeOH}$ $g_{cat}^{-1}$ $h^{-1}$.

In one embodiment, including any of the foregoing, the catalyst as described herein comprises between about 30 wt % to 60 wt % of copper oxide, between about 50 wt % to 62 wt % of zinc oxide, and between about 0.5 wt % to 10 wt % of lanthanum oxide on $Al_2O_3$ support and exhibits a $CO_2$ conversion of about 30% with a MeOH selectivity over carbon monoxide of about 42 wt % and a methanol yield of about 2.45 $g_{MeOH}$ $g_{cat}^{-1}$ $h^{-1}$ under the following specific conditions for about 5 hours: 1) a temperature of about 325°; 2) a molar ratio of $H_2:CO_2$ of about 4:1; a pressure range of about 85 bars; and, 4) a space velocity of about 55,000 $h^{-1}$.

In one embodiment, including any of the foregoing, the catalyst as described herein comprises between about 30 wt % to 60 wt % of copper oxide, between about 50 wt % to 62 wt % of zinc oxide, and about 1.0 wt % of lanthanum oxide on $Al_2O_3$ support and exhibits a $CO_2$ conversion of about 30% with a MeOH selectivity over carbon monoxide of about 42 wt % and methanol yield of about 2.45 $g_{MeOH}$ $g_{cat}^{-1}$ $h^{-1}$ under the following specific conditions for about 5 hours: 1) a temperature of about 325°; 2) a molar ratio of $H_2:CO_2$ of about 4:1; 3) a pressure range of about 85 bars; and, 4) a space velocity of about 55,000 $h^{-1}$.

In one embodiment, including any of the foregoing, the catalyst as described herein comprises about 30 wt % CuO/50 wt % ZnO/1 wt % $La_2O_3$ by weight on $Al_2O_3$ support and exhibits a $CO_2$ conversion of about 30% with a MeOH selectivity over carbon monoxide of about 42 wt % and methanol yield of about 2.45 $g_{MeOH}$ $g_{cat}^{-1}$ $h^{-1}$ under the following specific conditions for about 5 hours: 1) a temperature of about 325°; 2) a molar ratio of $H_2:CO_2$ of about 4:1; 3) a pressure range of about 85 bars; and, 4) a space velocity of about 55,000 $h^{-1}$.

Method for the Synthesis of Lanthanum Oxide-Promoted Cu-Based Catalysts Using a Combustion Synthesis Method The present invention also provides a simple method for the synthesis of lanthanum oxide promoted Cu-based catalysts/nanocomposites supported on alumina via a single step solution combustion synthesis.

The method for synthesizing lanthanum oxide promoted Cu-based catalysts/nanocomposites supported on alumina via a single step solution combustion synthesis comprises the steps of:
1) dissolving metal precursor nitrates in water and adding glycine;
2) stirring the mixture to afford a homogeneous mixture and heating the resulting solution over a hot plate for combustion that upon initiation, proceeds in an autothermal mode without any external heating source;
3) calcining the resultant powder to remove uncombusted precursor salts in air in a muffle furnace to afford the catalyst; and,
4) activating/reducing the catalyst prior to the hydrogenation of $CO_2$ by passing pure hydrogen stream over the catalyst.

In one embodiment, the metal precursor nitrates are copper nitrate trihydrate ($Cu(NO_3)_2 \cdot 3H_2O$), zinc nitrate hexahydrate ($Zn(NO_3)_2 \cdot 6H_2O$), aluminum nitrate nonahydrate ($Al(NO_3)_3 \cdot 9H_2O$), and lanthanum nitrate hexahydrate ($La(NO_3)_3 \cdot 6H_2O$).

In certain embodiments, including any of the foregoing, in step 4, the hydrogen stream is passed over the catalyst at a temperature in the range of about 300° C. to 550° C. or in the range of about 350° C. to 500° C. In one embodiment, in step 4, the hydrogen stream is passed over the catalyst at a temperature of about 350° C. In one embodiment, in step 4, the hydrogen stream is passed over the catalyst at a temperature of about 350° C. at a heating rate of 1° C.

In one embodiment, including any of the foregoing, the glycine/nitrate precursor molar ratio (glycine/oxidant ratio) is between about 0.1 and 1.5. In one embodiment, including any of the foregoing, the glycine/nitrate precursor ratio is between about 0.2 and 1.2. In one embodiment, including any of the foregoing, the glycine/nitrate precursor ratio is at least about 0.2. In one embodiment, including any of the foregoing, the glycine/nitrate precursor ratio is less than about 1.2. In one embodiment, including any of the foregoing, the glycine/nitrate precursor ratio is about 0.21.

In one embodiment, including any of the foregoing, the resultant powder is calcined at a temperature between about 300° C. to 850° C. In one embodiment, including any of the foregoing, the resultant powder is calcined at a temperature between about 400° C. to 800° C. In one embodiment, including any of the foregoing, the resultant powder is calcined at a temperature between about 400° C. to 600° C. In one embodiment, including any of the foregoing, the resultant powder is calcined at a temperature of about 400° C. In one embodiment, including any of the foregoing, the resultant powder is calcined in air for about 3 hours at 400° C. with a heating and cooling rate of 1° C.

In certain embodiments, including any of the foregoing, the catalyst described herein is tested for $CO_2$ hydrogenation in a temperature range between about 200° C. to 400° C. In certain embodiments, including any of the foregoing, the catalyst described herein is tested for $CO_2$ hydrogenation in a temperature range between about 250° C. to 350° C.

In certain embodiments, including any of the foregoing, the method described here affords a nanocomposite catalyst with a copper oxide loading in the range of about 20 wt % to 60 wt %. In certain embodiments, including any of the foregoing, the method described here affords a nanocomposite catalyst with a copper oxide loading in the range of about 30 wt % to 60 wt %. In certain embodiments, including any of the foregoing, the method described here affords a nanocomposite catalyst with a copper oxide loading in the range of about 20 to 50 wt %, about 20 to 40 wt %, about 30 wt % to 50 wt %, about 30 wt % to 50 wt %, or about 20 wt % to 30 wt %. In a preferred embodiment, the method described here affords a nanocomposite catalyst with a copper oxide loading of about 30 wt % copper oxide.

In certain embodiments, including any of the foregoing, the method described here affords a nanocomposite catalyst with a zinc oxide loading in the range of about 40 wt % to 65 wt %. In certain embodiments, including any of the foregoing, the method described here affords a nanocomposite catalyst with a zinc oxide loading in the range of about 50 wt % to 62 wt %. In certain embodiments, including any of the foregoing, the method described here affords a nanocomposite catalyst with a zinc oxide loading in the range of about 40 wt % to 60 wt %, about 40 wt % to 50 wt %, or about 50 wt % to 60 wt %. In a preferred embodiment, the method described here affords a nanocomposite catalyst with a zinc oxide loading of about 50 wt %.

In certain embodiments, including any of the foregoing, the method described here affords a nanocomposite catalyst with a lanthanum oxide loading in the range of about 0.5 wt % to 10.0 wt %. In certain embodiments, including any of the foregoing, the method described here affords a nanocomposite catalyst with a lanthanum oxide loading in the range of about 0.5 wt % to 8.0 wt %, about 0.5 wt % to 6.0 wt %, about 0.5 wt % to 4.0, about 0.5 wt % to 2.0 wt %, or about 0.5 wt % to 1.5 wt %. In certain embodiments, including any of the foregoing, the method described here affords a nanocomposite catalyst with a lanthanum oxide loading in the range of about 0.5 wt % to 3.0 wt %. In one embodiment, including any of the foregoing, the method described here affords a nanocomposite catalyst with a lanthanum oxide loading of at least about 0.5 wt %. In one embodiment, including any of the foregoing, the method described here affords a nanocomposite catalyst with a lanthanum oxide loading of less than about 10 wt % lanthanum oxide. In a preferred embodiment, including any of the foregoing, the method described here affords a nanocomposite catalyst with a lanthanum oxide loading of about 1 wt % lanthanum oxide.

In certain embodiments, including any of the foregoing, the method described here affords a nanocomposite catalyst with a copper oxide loading in the range of about 20 wt % to 60 wt %, a zinc oxide loading in the range of about 40 wt % to 65 wt %, and a lanthanum oxide is loading in the range of about 0.5 wt % to 10 wt %. In certain embodiments, including any of the foregoing, the method described here affords a nanocomposite catalyst with a copper oxide loading in the range of about 30 wt % to 60 wt %, a zinc oxide loading in the range of about 50 wt % to 62 wt %, and a lanthanum oxide loading in the range of about 0.5 wt % to 10 wt %. In certain embodiments, the method described here affords a nanocomposite catalyst with a copper oxide loading of about 30 wt % copper oxide, a zinc oxide loading of about 50 wt %, and a lanthanum oxide loading of about 1 wt %.

In certain embodiments, including any of the foregoing, the method described here affords a nanocomposite catalyst with a copper oxide loading in the range of about 20 wt % to 60 wt %, a zinc oxide loading in the range of about 40 wt % to 65 wt % of zinc oxide, and a lanthanum oxide loading in the range of about 0.5 wt % to 10 wt %. In certain embodiments, including any of the foregoing, the method described here affords a nanocomposite catalyst with a copper oxide loading in the range of about 30 wt % to 60 wt %, a zinc oxide loading in the range of about 50 wt % to 62 wt %, and a lanthanum oxide loading in the range of about 0.5 wt % to 10 wt %. In one embodiment, including any of the foregoing, the method described here affords a nanocomposite catalyst with a copper oxide loading of about 30 wt % copper oxide, a zinc oxide loading of about 50 wt %, and a lanthanum oxide loading of about 1 wt %.

In one embodiment, including any of the foregoing, the method described here affords a nanocomposite catalyst with a copper oxide loading between about 20 wt % to 60 wt %, a zinc oxide loading between about 40 wt % to 65 wt %, and a lanthanum oxide loading between about 0.5 wt % to 10 wt % on $Al_2O_3$ support. In one embodiment, including any of the foregoing, the method described here affords a nanocomposite catalyst with a copper oxide loading between about 30 wt % to 60 wt % copper oxide, a zinc oxide loading between about 50 wt % to 62 wt %, and a lanthanum oxide loading between about 0.5 wt % to 10 wt % on the $Al_2O_3$ support. In one embodiment, including any of the foregoing, the method described here affords a nanocomposite catalyst with a copper oxide loading of about 30 wt %, a zinc oxide loading of about 50 wt % zinc oxide, and a lanthanum oxide loading of about 1 wt % on $Al_2O_3$ support.

In a preferred embodiment, including any of the foregoing, the method described herein affords highly active and stable copper oxide-based nanocatalysts with a metal loading in the range between about 30 wt % to 60 wt % promoted with lanthanum oxide with a loading range between about 0.5 wt % to 10 wt % supported on alumina.

Figure 5A:
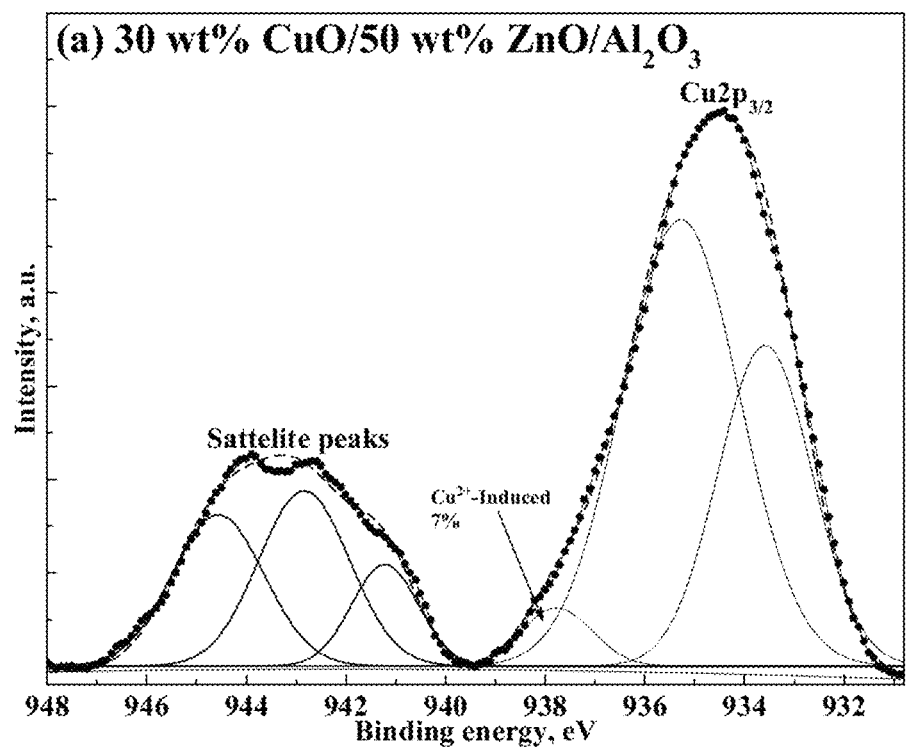
FIG. 5A is an X-ray photoelectron spectroscopy (XPS) analysis of unpromoted 30 wt % CuO/50 wt % ZnO/$Al_2O_3$ catalyst as described in Example 2.
Figure 5B:
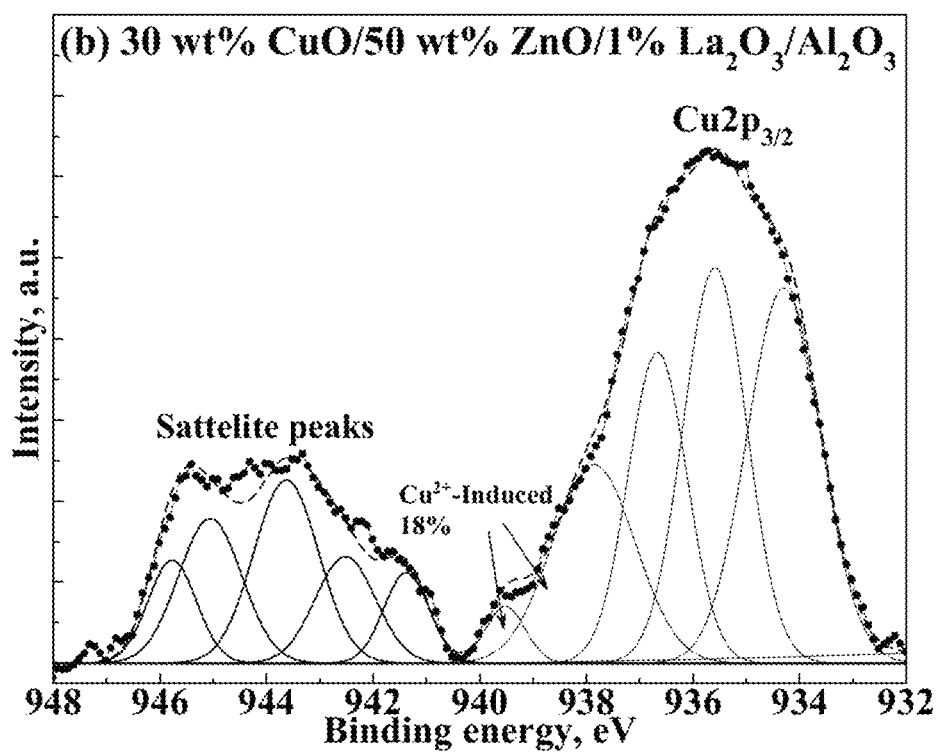
FIG. 5B is an X-ray photoelectron spectroscopy (XPS) analysis of lanthanum oxide promoted 30 wt % CuO/50 wt % ZnO/1 wt % $La_2O_3$/$Al_2O_3$ catalyst as described in Example 2.
Figure 6:
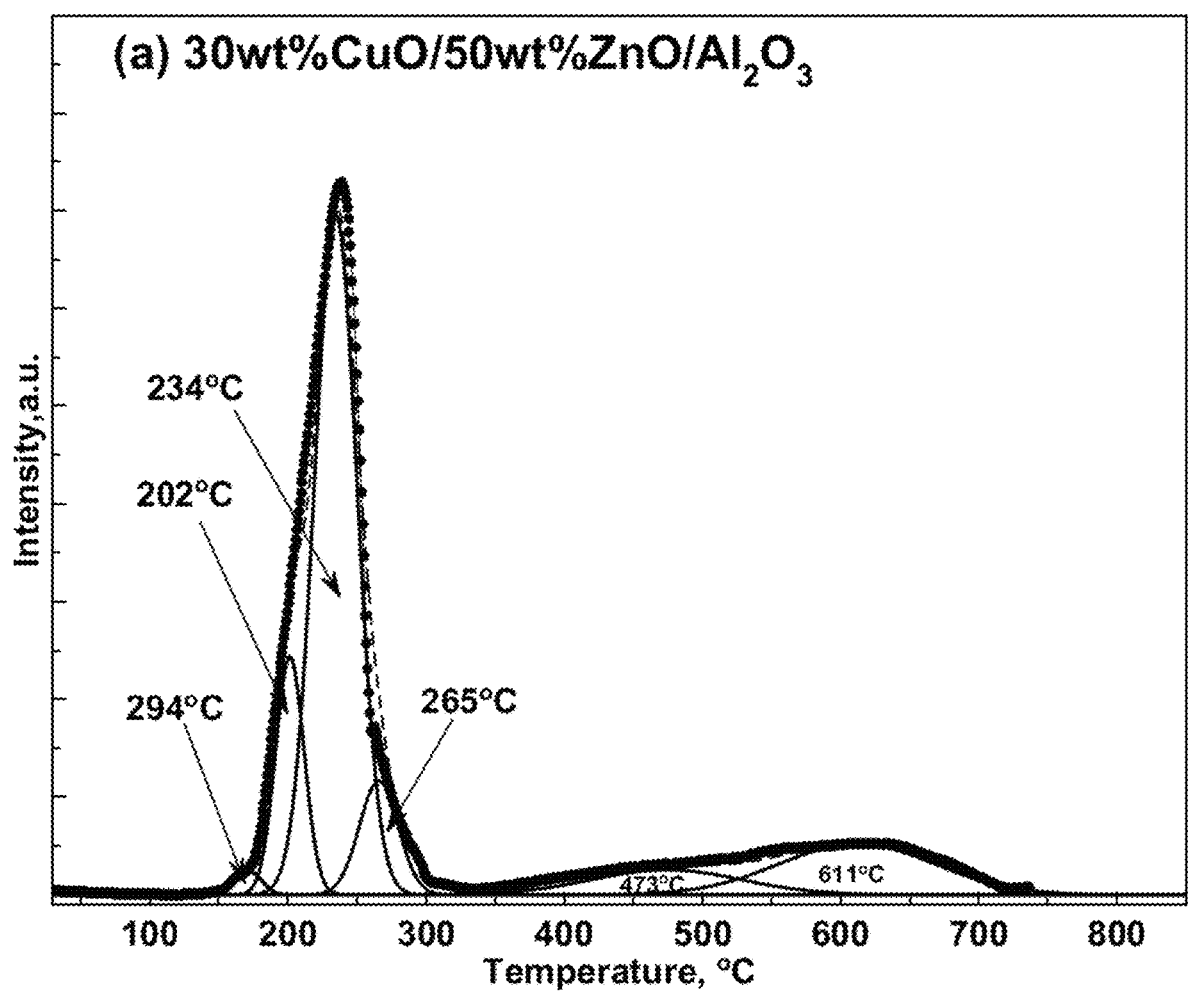
FIG. 6 is a temperature programmed reduction (TPR) profile of the unpromoted 30 wt % CuO/50 wt % ZnO/$Al_2O_3$ catalyst synthesized via the SCS method as described in Example 2.
Figure 7:
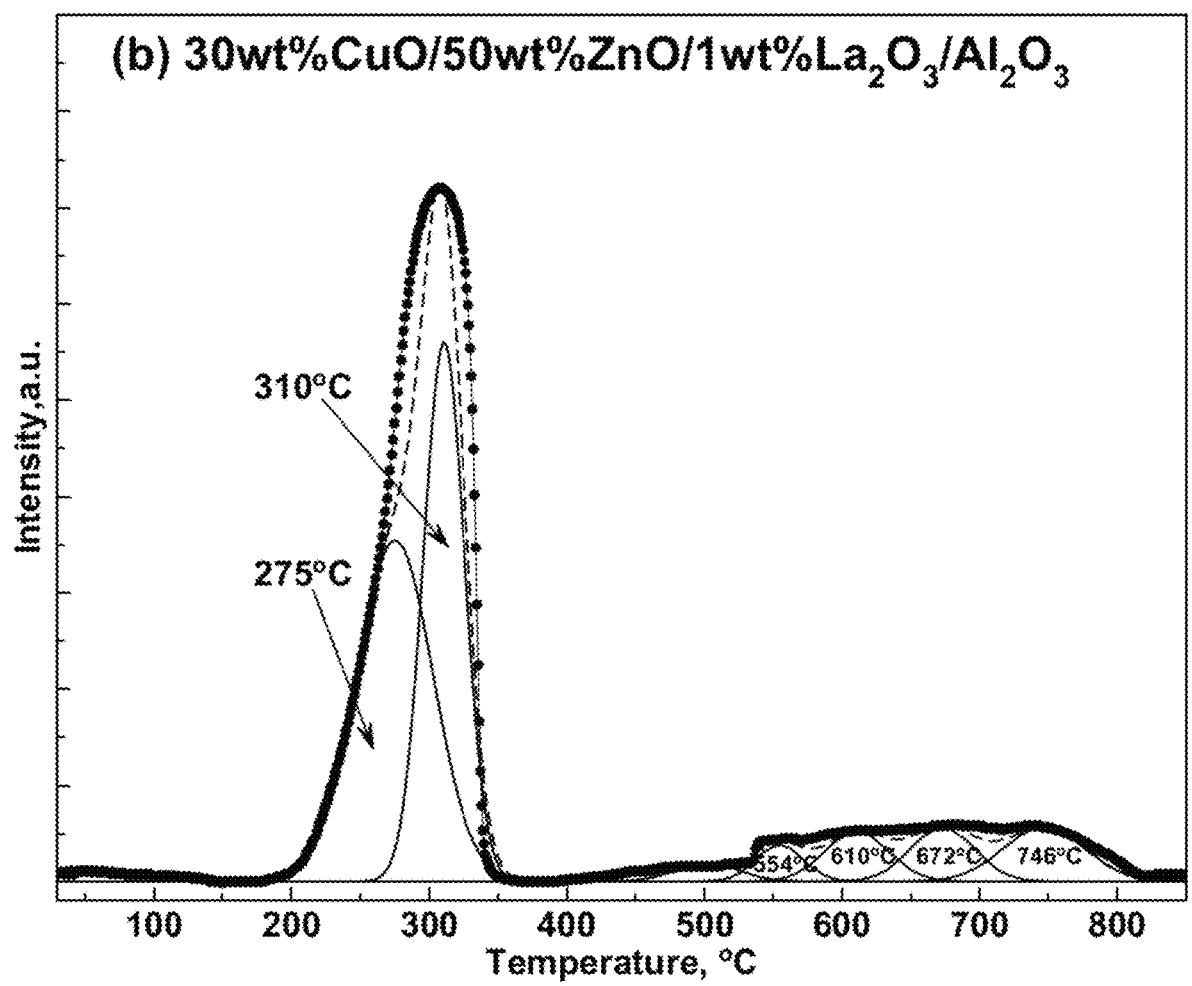
FIG. 7 is a temperature programmed reduction (TPR) profile of the lanthanum oxide promoted 30 wt % CuO/50 wt % ZnO/1 wt % $La_2O_3$/$Al_2O_3$ catalyst synthesized via the SCS method as described in Example 2.
Figure 8A:
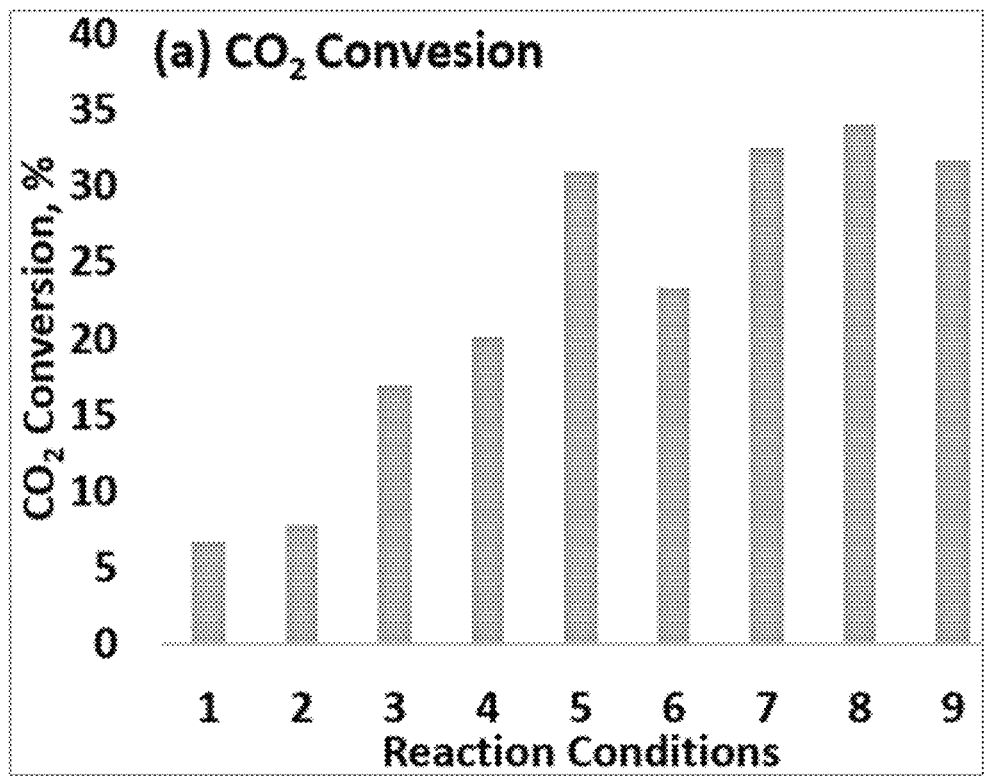
FIG. 8A illustrates the $CO_2$ conversion, measured in percent, of the 30 wt % CuO/50 wt % ZnO/1 wt % $La_2O_3$/$Al_2O_3$ catalyst at the various reaction conditions presented in Table 2 of Example 3.
Figure 8B:
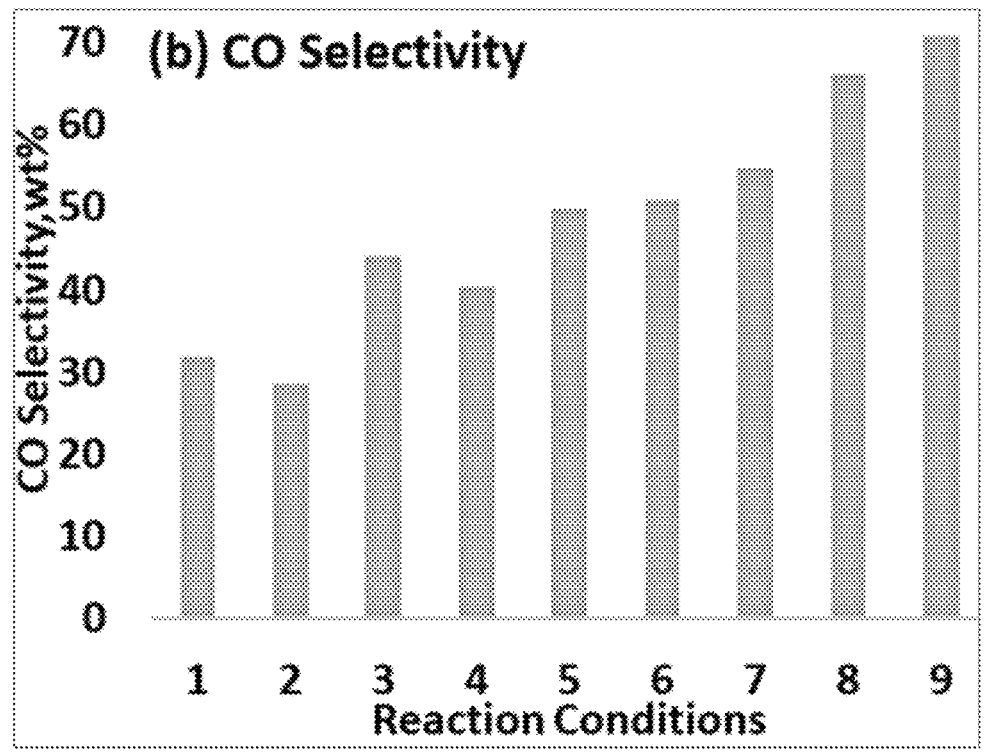
FIG. 8B illustrates the $CO_2$ selectivity, measured in weight percent, of the 30 wt % CuO/50 wt % ZnO/1 wt % $La_2O_3$/$Al_2O_3$ catalyst at the various reaction conditions presented in Table 2 of Example 3.
Figure 8C:
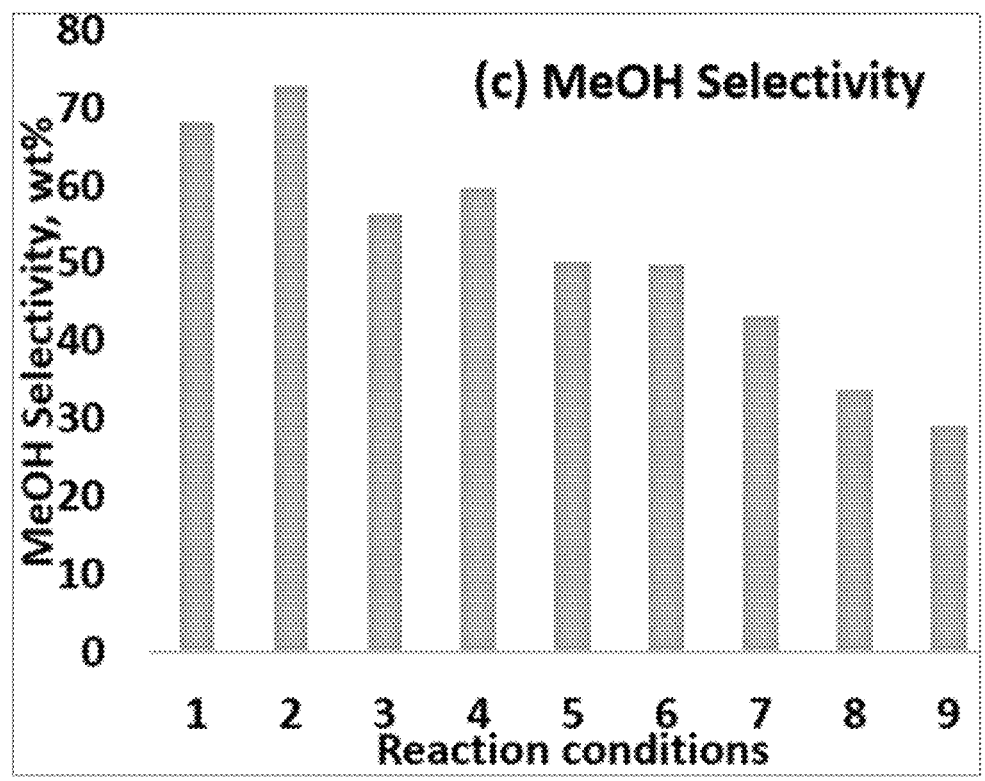
FIG. 8C illustrates the MeOH selectivity, measured in weight percent, of the 30 wt % CuO/50 wt % ZnO/1 wt % $La_2O_3$/$Al_2O_3$ catalyst at the various reaction conditions presented in Table 2 of Example 3.
Figure 8D:
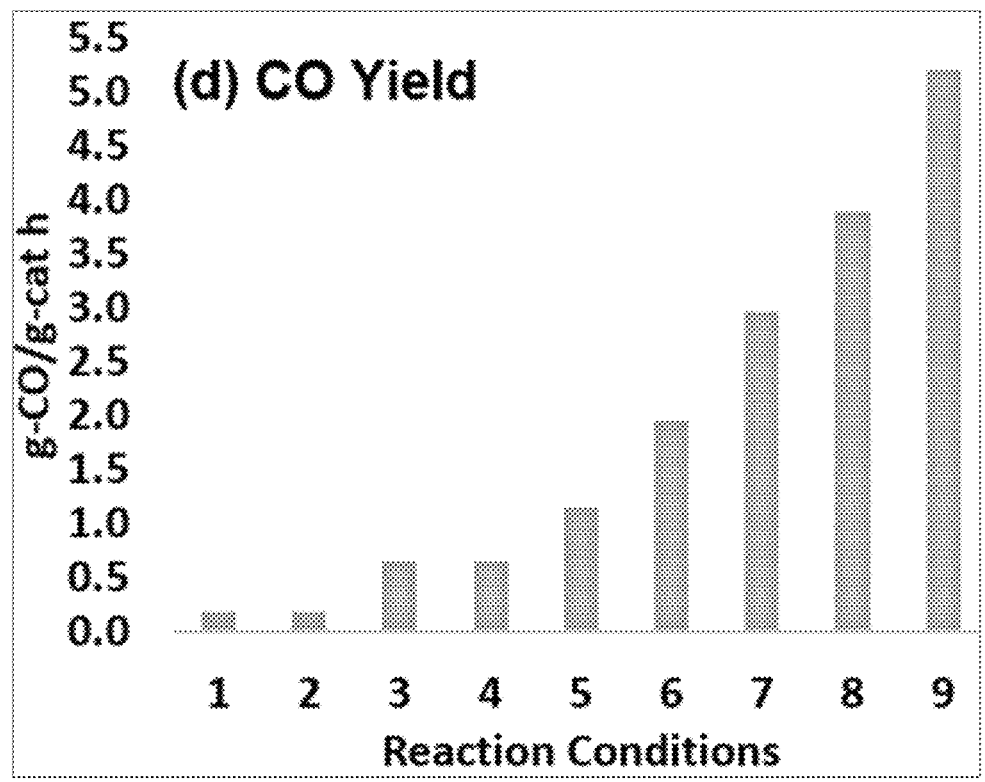
FIG. 8D illustrates the CO yield, measured in $g_{CO}$ $g_{cat}^{-1}$ $h^{-1}$, of the 30 wt % CuO/50 wt % ZnO/1 wt % $La_2O_3$/$Al_2O_3$ catalyst at the various reaction conditions presented in Table 2 of Example 3.
Figure 8E:
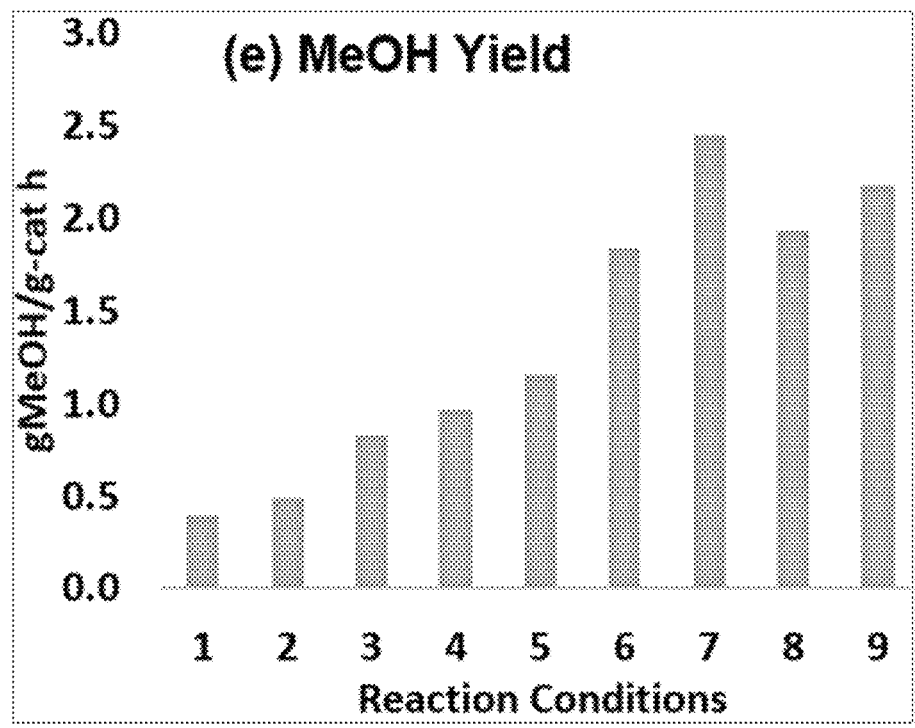
FIG. 8E illustrates the MeOH yield, measured in $g_{MEOH}$ $g_{cat}^{-1}$ $h^{-1}$, of the 30 wt % CuO/50 wt % ZnO/1 wt % $La_2O_3$/$Al_2O_3$ catalyst at the various reaction conditions presented in Table 2 of Example 3.

In certain embodiments, the addition of lanthanum oxide assists in controlling the catalytic performance, for example, the conversion percent and the selectivity for MeOH. This may be because incorporation of lanthanum oxide into the copper catalyst results in creating surface defects and oxygen vacancies without altering the metal particle size. For example, FIG. 6 is the temperature programmed reduction (TPR) profile of the unpromoted catalyst without lanthanum oxide and FIG. 7 is the TPR profile of the catalyst with 1 wt % of lanthanum oxide. The shift in reduction temperatures to higher degrees in the TPR of FIG. 7 indicates the presence of surface defects and oxygen vacancies compared to the TPR of FIG. 6. Additionally FIG. 5A is the XPS of the unpromoted catalyst without lanthanum oxide and FIG. 5B is the XPS of the catalyst with 1 wt % of lanthanum oxide. As shown in FIG. 5B compared to FIG. 5A, the addition of 1 wt % of lanthanum oxide resulted in an increase in the percentage of $Cu^{2+}$-induced phases. Therefore, in one embodiment, including any of the foregoing, the method described herein results in the creation of more oxygen vacancies and/or surface defects due to the incorporation of lanthanum oxide-induced electronic modifications. In one embodiment, the catalyst as described herein is characterized as exhibiting $Cu^{2+}$-induced phases of greater than about 7% as measured by XPS wherein the percentage of the induced phases is calculated based on total area of the integrated peaks. In certain embodiments, the catalyst as described herein is characterized as exhibiting $Cu^{2+}$-induced phases of greater than about 10%, greater than about 15%, greater than about 20%, or greater than about 25% as measured by XPS wherein the percentage of the induced phases is calculated based on total area of the integrated peaks. In one embodiment, the catalyst as described herein is characterized as exhibiting $Cu^{2+}$-induced phases of about 18% as measured by XPS wherein the percentage of the induced phases is calculated based on total area of the integrated peaks.

EXAMPLES

Abbreviations $Al_2O_3$ aluminum oxide
$CH_4$ methane
CO carbon monoxide
$CO_2$ carbon dioxide
CuO copper oxide
G/O Glycine/oxidant ratio or glycine/metal nitrate precursors ratio
$H_2$ dihydrogen
$La_2O_3$ lanthanum oxide
GHSV gas hourly space velocity
MeOH methanol
T.O.S. Time on Stream
ZnO zinc oxide

Example 1. General Synthesis of Lanthanum Oxide-Promoted Cu-Based Catalysts

In a typical preparation procedure, required amounts of metal precursor nitrates are dissolved in an appropriate amount of water in a 1000 mL beaker. The required amount of glycine is also added. This mixture is then stirred well to afford a homogeneous mixture and the resulting solution is heated over a hot plate for combustion. The reaction is exothermic in nature and once the combustion initiates, it proceeds in an auto-thermal mode without any external heating source.

After complete combustion of all precursors, the resultant powder is calcined in air at the appropriate temperature (400° C.) in a muffle furnace.

Example 2. The Effect of Glycine/Oxidant Ratio and Calcination Temperature on Unpromoted Cu-Based Catalysts Eight unpromoted 30 wt % CuO/50 wt % $ZnO/Al_2O_3$ catalysts were synthesized with various glycine/nitrate precursor (glycine/oxidants, G/O) ratios. The catalysts were synthesized according to the general procedure in Example 1. Each sample was prepared with 9.1 g of $Cu(NO_3)_2·3H_2O$, 18.15 g of $Zn(NO_3)_2·6H_2O$, and 14.12 g of $Al(NO_3)_3·9H_2O$ dissolved in 100 mL of $H_2O$. The amount of glycine for each catalyst is provided in Table 1. The samples were calcined at 600° C.

TABLE 1

Glycine amount to prepare unpromoted
30 wt % CuO/50 wt % $ZnO/Al_2O_3$
catalysts of FIG. 1 with various G/O ratios

| Molar ratio of G/O | Glycine (g) |
| --- | --- |
| 1.236 | 28.80 |
| 0.927 | 21.60 |
| 0.804 | 18.72 |
| 0.747 | 17.20 |
| 0.618 | 14.40 |
| 0.309 | 7.20 |
| 0.258 | 6 |
| 0.206 | 4.80 |

Figure 2:
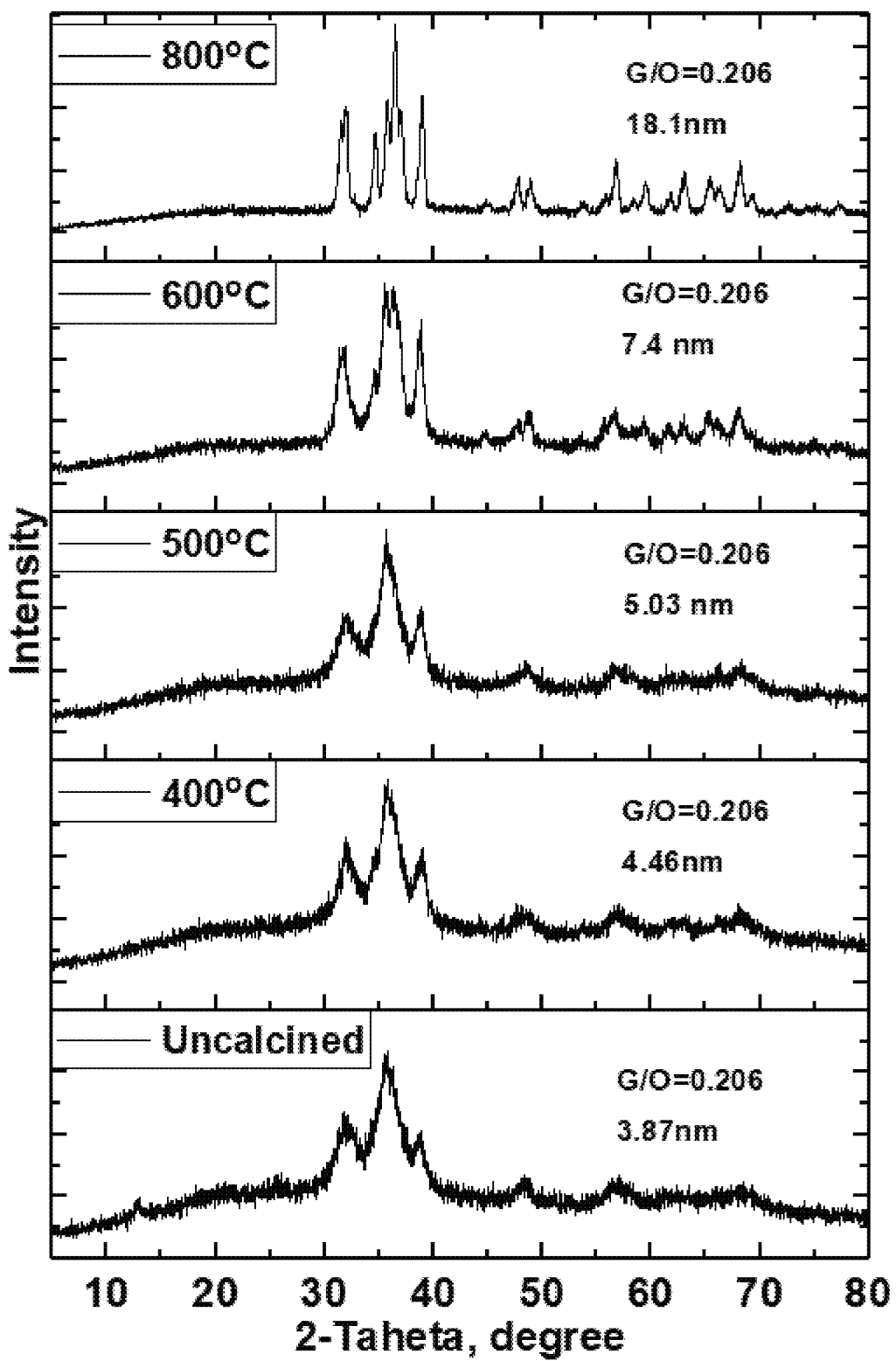
FIG. 2 provides X-ray diffraction patterns of unpromoted 30 wt % CuO/50 wt % ZnO/$Al_2O_3$ catalysts calcined at various temperatures as described in Example 1.

The characterization and catalytic test results for nanocatalysts are provided below. The X-ray diffraction patterns for each catalyst demonstrate the effects of G/O (glycine/oxidants) molar ratio on the particle size (FIG. 1). By varying the G/O ratio, the size of the nanoparticles was modified. The lower the glycine/oxidant ratio, the smaller the nanoparticle. For example, a G/O molar ratio of 0.206 resulted in comparatively smaller and well dispersed nanoparticles (4.46 nm). For this reason, the G/O molar ratio of 0.206 was held constant in the next study where the effect of calcination temperature on particle size was study. As shown in FIG. 2, as calcination temperature was lowered from 800° C. to 400° C., the particle size decreased.

Example 3. Characterization of Promoted Cu-Based Catalysts

Three promoted 30 wt % CuO/50 wt % $ZnO/1$ wt % $La_2O_3/Al_2O_3$ catalysts were synthesized with various G/O (glycine/oxidants) molar ratios. The samples were calcined at 600° C. The catalysts were synthesized according to the general procedure in Example 1. Each sample was prepared with 9.1 g of $Cu(NO_3)_2·3H_2O$, 18.15 g of $Zn(NO_3)_2·6H_2O$, 0.2656 g of $La(NO_3)_3·6H_2O$, and 13.42 g of $Al(NO_3)_3·9H_2O$ dissolved in 100 mL of $H_2O$. The amount of glycine for the catalysts prepared with a G/O molar ratio of 1.2, 0.6, and 0.2 was the same as the amount shown in Table 1.

Figure 3A:
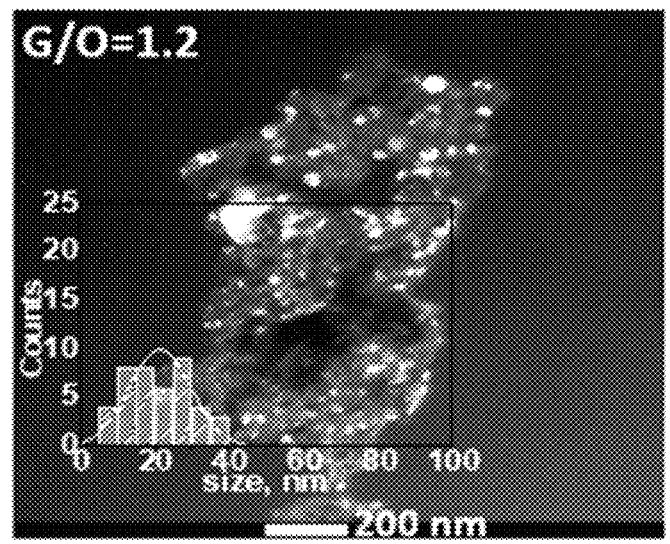
FIG. 3A is TEM image of the 30 wt % CuO/50 wt % ZnO/1 wt % $La_2O_3$/$Al_2O_3$ catalyst produced with a glycine/oxidant molar ratio (G/O) of 1.2 as described in Example 2. The sample was calcined at 600° C. TEM analysis affirmed XRD findings of FIGS. 5A and 5B.
Figure 3B:
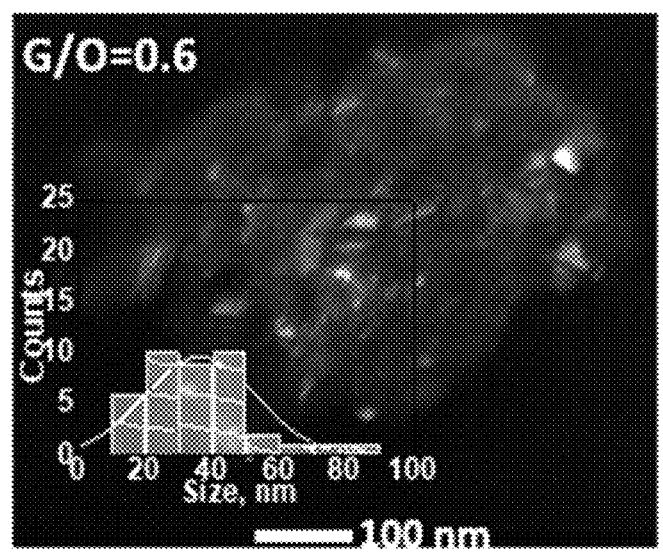
FIG. 3B is TEM image and analysis of the 30 wt % CuO/50 wt % ZnO/1 wt % $La_2O_3$/$Al_2O_3$ catalyst produced with a glycine/oxidant molar ratio (G/O) of 0.6 as described in Example 2. The sample was calcined at 600° C. TEM analysis affirmed XRD findings of FIGS. 5A and 5B.
Figure 3C:
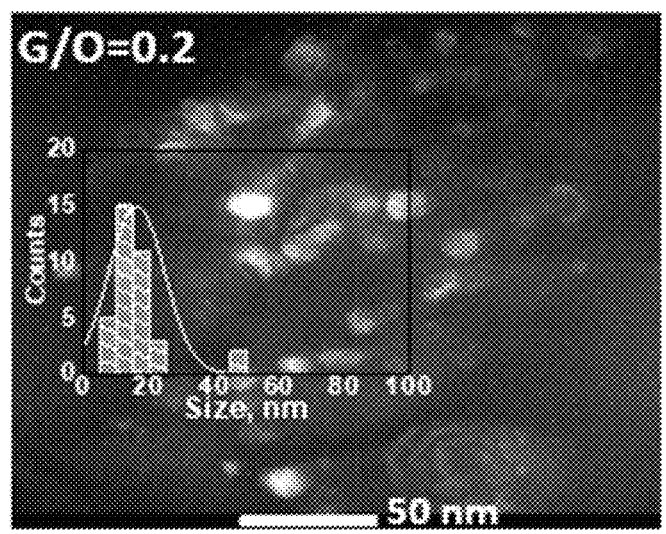
FIG. 3C is TEM image and analysis of the 30 wt % CuO/50 wt % ZnO/1 wt % $La_2O_3$/$Al_2O_3$ catalyst produced with a glycine/oxidant molar ratio (G/O) of 0.206 as described in Example 2. The sample was calcined at 600° C.
Figure 4A:
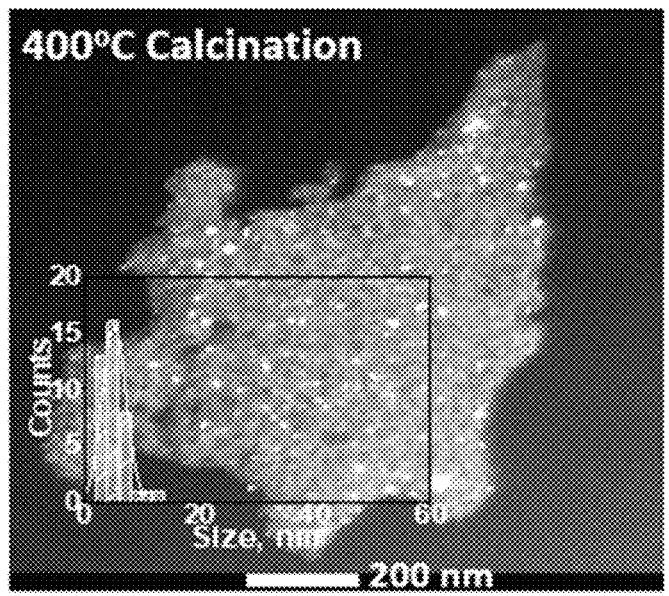
FIG. 4A is a TEM image and analysis of the 30 wt % CuO/50 wt % ZnO/1 wt % $La_2O_3$/$Al_2O_3$ catalyst produced with a glycine/oxidant molar ratio (G/O) of 0.206 calcined at 400° C. as described in Example 2.
Figure 4B:
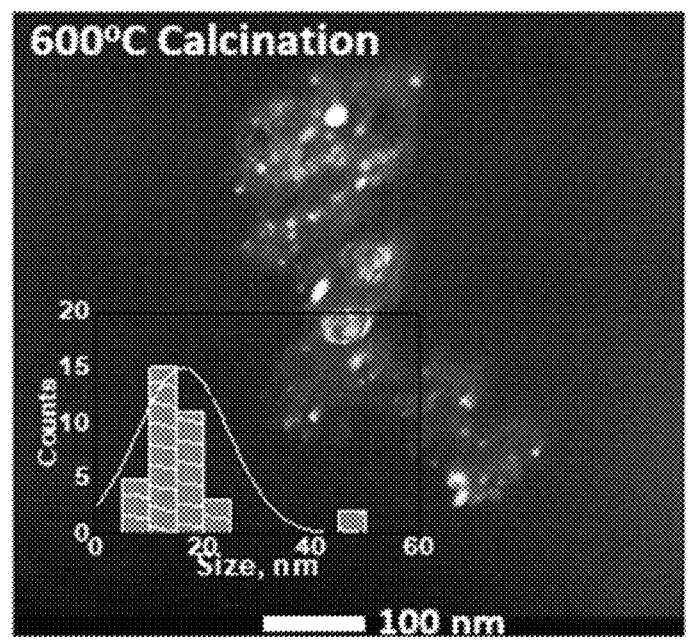

TEM images for the promoted 30 wt % CuO/50 wt % ZnO/1 wt % $La_2O_3/Al_2O_3$ catalysts prepared with varying amounts of glycine are shown in FIGS. 3A-3C. As shown in FIGS. 3A-3C, a fuel deficient mixture (lower G/O molar ratio) resulted in smaller average particle size. For example, the sample prepared with G/O molar ratio of 0.206 (FIG. 3C) resulted in an average particle size of 6.4 nm. TEM images for the promoted 30 wt % CuO/50 wt % ZnO/1 wt % $La_2O_3/Al_2O_3$ catalysts calcined at 400° C. and 600° C. are shown in FIG. 4A and FIG. 4B, respectively. Calcination at 400° C. was effective for combustion and resulted in a minimal increase in particle size.

FIG. 5A and FIG. 5B demonstrate the effects of lanthanum oxide incorporation into the catalyst. FIG. 5A is the X-ray photoelectron spectroscopy (XPS) analysis of unpromoted 30 wt % CuO/50 wt % ZnO/$Al_2O_3$ catalyst and FIG. 5B is the X-ray photoelectron spectroscopy (XPS) analysis of lanthanum oxide promoted 30 wt % CuO/50 wt % ZnO/1% $La_2O_3/Al_2O_3$. As shown in FIG. 5B compared to FIG. 5A, with incorporation of lanthanum oxide, an increase in the percentage of induced phases was recorded. The percentage of induced peaks in the unpromoted catalyst (FIG. 5A) was only 7%, while the percentage in the promoted catalyst (FIG. 5B) was 18%. The percentage of these phases is calculated based on total area of the integrated peaks.

The effect of lanthanum oxide addition is also shown in FIG. 6 and FIG. 7. FIG. 6 is the temperature programmed reduction (TPR) profile of the unpromoted catalyst (30 wt % CuO/50 wt % ZnO/$Al_2O_3$) and FIG. 7 is the temperature programmed reduction (TPR) profile of the lanthanum oxide promoted catalyst (30 wt % CuO/50 wt % ZnO/1 wt % $La_2O_3/Al_2O_3$). As shown in FIG. 7 compared to FIG. 6, a shift in reduction temperature to higher degrees was recorded for the lanthanum oxide promoted catalyst, indicating an increase in stronger metal support interaction and the presence of surface defects and/or oxygen vacancies.

Example 4. Catalytic Performance of 30 wt % CuO/50 wt % ZnO/1 wt % $La_2O_3/Al_2O_3$ Catalyst The catalytic performance of the lanthanum oxide promoted 30 wt % CuO/50 wt % ZnO/1 wt % $La_2O_3/Al_2O_3$ catalyst prepared with a G/O molar ratio of 0.206 and calcined at 400° C. was evaluated in a high-pressure lab-scale test unit (PID, Micromeritics) under various conditions.

The unit was equipped with three gas lines controlled by high accuracy mass flow controllers and it operated with a stainless steel and hastelloy fixed bed reactor (ID: 9.3 mm), externally heated with a three-zone furnace. The exit stream of the reactor was cooled via a paltrier cold trap and was directed to a system of vessel for the separation and collection of the liquid and gaseous products. The reaction temperature was monitored with a thermocouple inserted in the catalytic bed. The gaseous products were analyzed using an on-line GC-TCD. The liquids were collected in a trap (5° C.) and were analyzed offline. The analysis was performed with a GC Agilent 7890A equipped with FID detectors.

Catalytic test results under the parameters in Table 2 are shown in FIGS. 8A-8E. The highest yield of MeOH recorded was under Condition 7 where the temperature was 325° C., the pressure was 85 bar; the gas hourly space velocity was 55,000 $h^{-1}$, and the $H_2/CO_2$ molar ratio was 4:1.

TABLE 2

Conditions for Catalytic Performance Evaluations

| | Parameters/Conditions | | | |
|---|---|---|---|---|
| Condition | Temperature (° C.) | Pressure (bar) | Gas Hourly Space Velocity ($h^{-1}$) | $H_2/CO_2$ Molar Ratio |
| 1 | 250 | 60 | 27,000 | 3.43 |
| 2 | 250 | 85 | 27,000 | 3.43 |
| 3 | 250 | 85 | 27,000 | 3.43 |
| 4 | 275 | 65 | 27,000 | 4 |
| 5 | 300 | 85 | 27,000 | 4 |
| 6 | 300 | 85 | 55,000 | 4 |
| 7 | 325 | 85 | 55,000 | 4 |
| 8 | 350 | 85 | 55,000 | 4 |
| 9 | 350 | 85 | 55,000 | 4 |

Figure 9A:
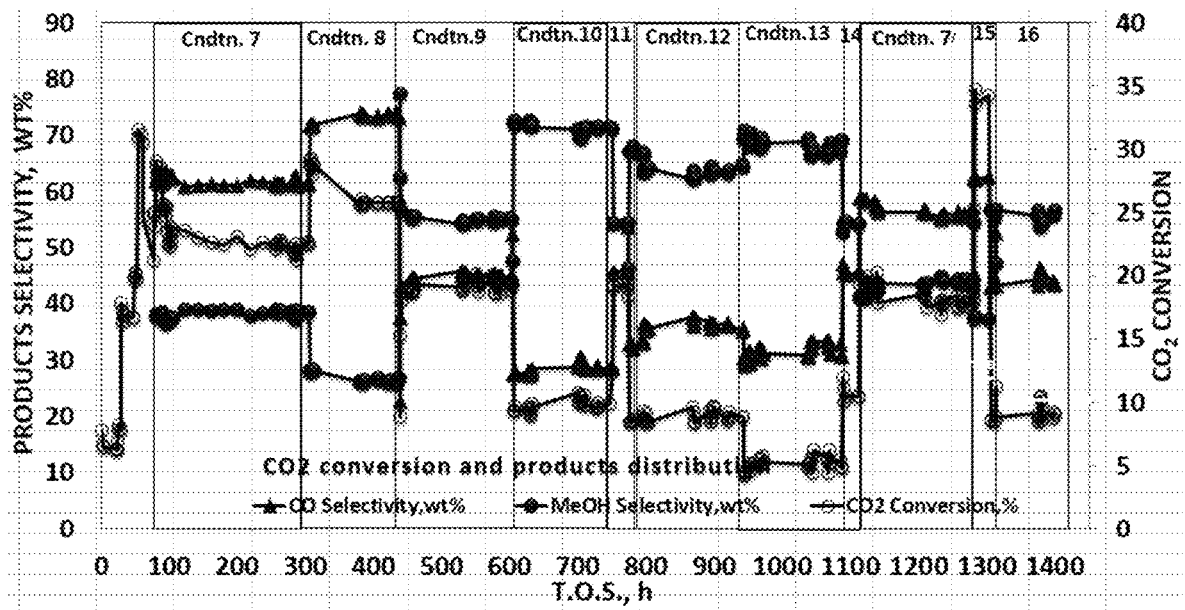
FIG. 9A illustrates the $CO_2$ selectivity, the MeOH selectivity, and the $CO_2$ conversion percentage of the 30 wt % CuO/50 wt % ZnO/1 wt % $La_2O_3$/$Al_2O_3$ catalyst for reaction conditions 7-16 for the T.O.S. (time on stream) stability test as described in Example 4.
Figure 9B:
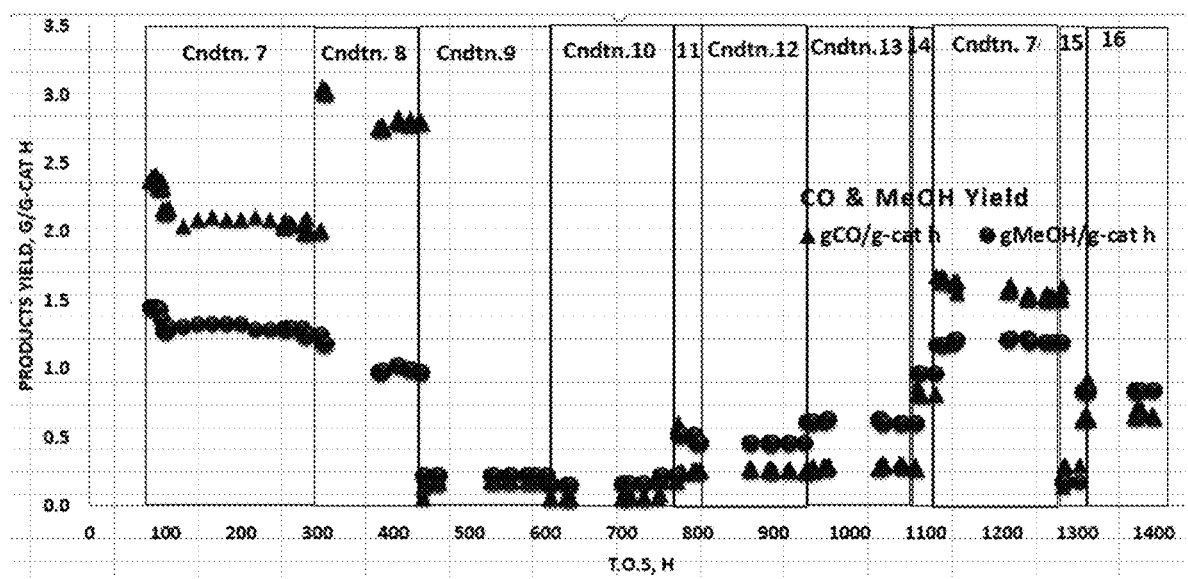
FIG. 9B illustrates the CO and MeOH yield of the 30 wt % CuO/50 wt % ZnO/1 wt % $La_2O_3$/$Al_2O_3$ catalyst at reaction conditions 7-16 for the T.O.S. (time on stream) stability test as described in Example 4.

Example 4. Stability Test of 30 wt % CuO/50 wt % ZnO/1 wt % $La_2O_3/Al_2O_3$ Catalyst For the stability test, the 30 wt % CuO/50 wt % ZnO/1 wt % $La_2O_3/Al_2O_3$ catalyst was first activated following the same procedure described on pages 15-16. This activation was performed by heating the catalyst to 350° C. in a gaseous stream of pure hydrogen at a ramp of 1° C. with a dwell time of three hours. The catalyst was then cooled down to the initial conditions described in Condition 1 in Table 3 (250° C.). This was followed by switching the flow to the required composition of reactants mixture gas and increasing the pressure to 60 bars (Condition 1 of Table 3). The conditions were changed over time according to Table 3. The CO selectivity, the MeOH selectivity, and the $CO_2$ conversion for conditions 7-16 are shown in FIG. 9A. The CO and MeOH yield for conditions 7-16 are shown in FIG. 9B.

TABLE 3

Parameters and Conditions of Stability Test

| | Parameters/Conditions | | | |
|---|---|---|---|---|
| Condition | Temperature (° C.) | Pressure (bar) | Gas Hourly Space Velocity ($h^{-1}$) | $H_2/CO_2$ Molar Ratio |
| 1 | 250 | 60 | 27,000 | 3.43 |
| 2 | 250 | 85 | 27,000 | 3.43 |
| 3 | 275 | 85 | 27,000 | 3.43 |
| 4 | 275 | 85 | 27,000 | 4 |
| 5 | 300 | 85 | 27,000 | 4 |
| 6 | 300 | 85 | 54,000 | 4 |
| 7 | 325 | 85 | 54,000 | 4 |
| 7' | 325 | 85 | 54,000 | 4 |
| 8 | 350 | 85 | 54,000 | 4 |
| 9 | 275 | 85 | 7,000 | 4 |
| 10 | 250 | 85 | 7,000 | 4 |
| 11 | 275 | 85 | 7,000 | 4 |
| 12 | 275 | 85 | 27,000 | 4 |
| 13 | 275 | 85 | 54,000 | 4 |
| 14 | 300 | 85 | 54,000 | 4 |
| 15 | 325 | 85 | 5,400 | 4 |
| 16 | 300 | 85 | 54,000 | 4 |

The previous detailed description is of a small number of embodiments for implementing the invention and is not intended to be limiting in scope. One of skill in the art will immediately envisage the methods and variations used to implement this invention in other areas than those described in detail. The following claims set forth a number of embodiments of the invention disclosed with greater particularity.

What is claimed:

1. A lanthanum oxide-promoted Cu-based nanocomposite catalyst for $CO_2$ hydrogenation to methanol comprising:
   (a) Nanoparticulates in the size range of about 3 nm to 20 nm comprising:
      (1) a copper oxide loading of about 20 wt % to 60 wt %;
      (2) a zinc oxide loading of about 40 wt % to 65 wt %; and
      (3) a lanthanum oxide with a loading of about 0.5 wt % to 10 wt %; and,
   (b) Alumina as support; and
wherein the catalyst has a BET surface area of about 77 $mg^2/g$.

2. The catalyst of claim 1, comprising:
   (1) a copper oxide loading of about 30% wt % to 60 wt %;
   (2) a zinc oxide loading of about 50 wt % to 62 wt %; and
   (3) a lanthanum oxide loading between about 0.5 wt % to 10 wt %.

3. The catalyst of claim 1, wherein the copper oxide loading is about 30 wt %.

4. The catalyst of claim 1, wherein the zinc oxide loading is about 50 wt %.

5. The catalyst of claim 1, wherein the lanthanum oxide loading is about 0.5 wt % to 5 wt %.

6. The catalyst of claim 1, wherein the lanthanum oxide loading is about 1 wt %.

7. The catalyst of claim 1, wherein the catalyst exhibits a MeOH yield of about 2.5 $g_{MeOH}$ $g_{cat}^{-1}$ $h^{-1}$ under the conditions of 1) a temperature of about 325° C.; 2) a pressure of about 85 bars; 3) a $H_2:CO_2$ ratio of about 3:1 to 4:1; and, 4) a gas hourly space velocity of between about 7,000 and 55,000 $h^{-1}$.

8. The catalyst of claim 7, wherein the $H_2:CO_2$ ratio is about 4:1.

9. The catalyst of claim 7, wherein the gas hourly space velocity is between about 27,000 and 55,000 $h^{-1}$.

10. The catalyst of claim 7, wherein the catalyst exhibits a MeOH selectivity of about 42 wt %.

11. The catalyst of claim 7, wherein the catalyst exhibits a $CO_2$ conversion of about 30%.

12. The catalyst of claim 1, wherein the catalyst exhibits $Cu^{2+}$-induced phases of about 18% as measured by XPS, wherein the percentage of the induced phases is calculated based on total area of the integrated peaks.

13. A method for the synthesis of the nanocomposite catalyst of claim 1, wherein the synthesis is a single-step solution combustion synthesis.

14. The method of claim 13, wherein copper oxide is loaded on the alumina in the range of 30-60 wt %.

15. The method of claim 13, wherein zinc oxide is loaded on the alumina in the range of 50 wt % to 62 wt %.

16. The method of claim 13, wherein lanthanum oxide is loaded on the alumina in the range of 0.5 wt % to 3 wt %.

17. The method of claim 13, wherein about 1 wt % of lanthanum oxide is loaded on the alumina.

18. The method of claim 13, wherein the single-step solution combustion synthesis comprises the steps:
   1) dissolving metal precursor nitrates in water and adding glycine to obtain a mixture wherein the nitrates are copper nitrate trihydrate ($Cu(NO_3)_2 \cdot 3H_2O$), zinc nitrate hexahydrate ($Zn(NO_3)_2 \cdot 6H_2O$), aluminum nitrate nonahydrate ($Al(NO_3)_3 \cdot 9H_2O$), and lanthanum nitrate hexahydrate ($La(NO_3)_3 \cdot 6H_2O$);
   2) stirring the mixture to form a homogeneous mixture and heating the homogeneous mixture over a hot plate for combustion to obtain nanocomposites;
   3) calcining the nanocomposites to remove uncombusted metal precursor nitrates in air in a muffle furnace to obtain the nanocomposite catalyst; and
   4) activating/reducing the nanocomposite catalyst by passing pure hydrogen stream over the nanocomposite catalyst.

19. The method of claim 18, wherein the glycine:metal precursor nitrates ratio is in the range of about 0.2:1 to 1.2:1.

20. The method of claim 18, wherein calcining the nanocomposites is performed at a temperature between about 400° C. to 800° C.

21. The method of claim 18, wherein the nanocomposite catalyst in step 4) comprises nanoparticles with a size of 6.4 nm.

22. The method of claim 18, wherein the nanocomposite catalyst in step 4) exhibits more oxygen vacancies and/or surface defects compared to a nanocomposite catalyst that does not comprise lanthanum oxide.

23. The method of claim 22, wherein the nanocomposite catalyst in step 4) exhibits $Cu^{2+}$-induced phases of about 18% as measured by XPS, wherein the percentage of the induced phases is calculated based on total area of the integrated peaks.

24. The method of claim 18, wherein step 4) is conducted between about 350° C. to 500° C.

* * * * *